(12) United States Patent
Sasian et al.

(10) Patent No.: US 7,580,118 B2
(45) Date of Patent: *Aug. 25, 2009

(54) METHODS, APPARATUS, AND SYSTEMS FOR EVALUATING GEMSTONES

(75) Inventors: Jose Sasian, Tucson, AZ (US); James Caudill, Las Vegas, NV (US); Peter Yantzer, Las Vegas, NV (US)

(73) Assignee: American Gem Society, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/125,364

(22) Filed: May 22, 2008

(65) Prior Publication Data

US 2008/0218730 A1    Sep. 11, 2008

Related U.S. Application Data

(63) Continuation of application No. 11/018,742, filed on Dec. 20, 2004, now Pat. No. 7,420,657, and a continuation of application No. 11/018,743, filed on Dec. 20, 2004, now Pat. No. 7,382,445.

(60) Provisional application No. 60/532,201, filed on Dec. 22, 2003, provisional application No. 60/563,025, filed on Apr. 16, 2004, provisional application No. 60/607,191, filed on Sep. 3, 2004.

(51) Int. Cl.
*G01N 21/01* (2006.01)
(52) U.S. Cl. ...................................... 356/30
(58) Field of Classification Search .................. 356/30, 356/416, 419
See application file for complete search history.

(56) References Cited

U.S. PATENT DOCUMENTS 5,966,673 A * 10/1999 Shannon, Sr. ................ 702/35
7,372,552 B2 * 5/2008 Sasian et al. .................. 356/30

* cited by examiner

*Primary Examiner*—L. G Lauchman
(74) *Attorney, Agent, or Firm*—Lewis, Rice & Fingersh, L.C.

(57) ABSTRACT

Methods for grading gemstones, apparatus for grading gemstones, and systems that utilize such methods and apparatus are disclosed.

6 Claims, 20 Drawing Sheets

METHODS, APPARATUS, AND SYSTEMS FOR EVALUATING GEMSTONES

CROSS REFERENCE TO RELATED APPLICATIONS

This application is a Continuation of U.S. patent application Ser. No. 11/018,742, filed Dec. 20, 2004 and now U.S. Pat. No. 7,420,657, and is a Continuation of U.S. patent application Ser. No. 11/018,743, filed Dec. 20, 2004 now U.S. Pat. No. 7,382,445. Both the above patents in turn claim benefit of U.S. Provisional Patent Application Ser. No. 60/532,201 filed on Dec. 22, 2003, U.S. Provisional Patent Application Ser. No. 60/563,025 filed on Apr. 16, 2004, and U.S. Provisional Patent Application Ser. No. 60/607,191 filed on Sep. 3, 2004. The entire contents of all the above documents are herein incorporated by reference.

BACKGROUND OF THE INVENTION

1. Field of the Invention

This invention relates to methods for grading gemstones, apparatus for grading gemstones, and systems that utilize such methods and apparatus.

2. Description of Related Art

Diamonds are often graded according to four "C's," which correspond to the diamond's color, clarity, carat weight, and cut. Color generally refers to the diamonds hue, and is related to impurities in the diamond's composition. Clarity generally refers to defects, such as bulk or surface defects, which can scatter light and reduce a diamond's visual appeal. The cut generally refers to both the diamond's shape (e.g., round, marquise, oval, etc.), and also to the diamond's proportions, symmetry, and polish. These parameters influence how light interacts with the diamond, which facets appear bright to an observer, which facets appear dark, and which facets appear colored.

SUMMARY

The invention relates to methods for grading gemstones, apparatus for grading gemstones, and systems that utilize such methods and apparatus. Grades can be used to establish the commercial value of gemstones.

In general, in a first aspect, the invention features a method that includes illuminating a gemstone with light from different directions, wherein light incident on the gemstone from a first range of ray directions and a second range of ray directions have a first color and a second color, respectively, and the first and second ranges and first and second colors are different, acquiring an image of the gemstone while illuminating the gemstone, and analyzing the image of the gemstone to provide information related to the quality of the gemstone based on the analysis.

Embodiments of the method can include one or more of the following features and/or features of other aspects.

The first range of ray directions can correspond to light incident on the gemstone from polar angles from about 45° to about 75° with respect to a hemispherical reference frame centered on the gemstone. The second range of ray directions can correspond to light incident on the gemstone from polar angles of about 75° or more with respect to the hemispherical reference frame Light incident on the gemstone from a third range of ray directions can have a third color, and the first, second, and third ranges and first, second, and third colors are different. The third range of ray directions can correspond to light incident on the gemstone from polar angles of about 45° or less with respect to the hemispherical reference frame. The first, second, and third colors are complimentary colors. The first, second, and third colors can be red, blue, and green, respectively.

The gemstone can have a table normal to a polar axis of the hemispherical reference frame. The gemstone can have a table oriented at a non-normal angle with respect to a polar axis of the hemispherical reference flame.

Analyzing the image can include determining a proportion of the image comprising the first color. The information provided related to the quality of the gemstone can include a grade based on the proportion of the image comprising the first color, Analyzing the image can further include determining a proportion of the image comprising the second color. The information provided related to the quality of the gemstone can include a grade based on a proportion of the image comprising the first and second colors. Light incident on the gemstone from a third range of ray directions can have a third color, and the first, second, and third ranges and first, second, and third colors are different, and wherein analyzing the image can include determining a proportion of the image comprising the third color. The information provided related to the quality of the gemstone can include a grade based on a proportion of the image comprising the first and third colors. Analyzing the image can include determining a proportion of the image comprising neither the first, second, or third colors. Evaluating the gemstone can further include assigning the gemstone a grade based on the proportion of the image including neither the first, second, or third colors.

The image can be acquired at 90° with respect to a hemispherical reference frame centered on the gemstone. The image can be acquired from a location between about one centimeter and about 100 centimeters from the gemstone. The location can be between about 20 centimeters and about 30 centimeters from the gemstone (e.g., about 25 centimeters from the gemstone).

The gemstone can be a diamond, such as a fancy cut diamond.

In general, in another aspect, the invention features a system including an illumination apparatus for illuminating a gemstone with light from different ray directions, wherein light incident on the gemstone from a first range of ray directions and a second range of ray directions have a first color and a second color, respectively, and the first and second ranges and first and second colors are different. The system also includes an imaging device positioned relative to the illumination apparatus to acquire an image of the gemstone while the illumination device illuminates the gemstone, and an electronic controller in communication with the imaging device which during operation analyzes the image of the gemstone and provides information related to the quality of the gemstone based on the analysis.

Embodiments of the system can include one or more of the following features and/or features of other aspects.

The illumination apparatus can include a housing, and an inner surface of the housing can include a portion having the first color and a portion having the second color. Light incident on the gemstone from a third range of ray directions can have a third color, and the first, second, and third ranges and first, second, and third colors can be different. The inner surface can further include a portion having the third color. The first, second, and third colors can be complimentary colors (e.g., the first, second, and third colors can be red, green, and blue, respectively). The first range of ray directions can correspond to light reflected from the portion of the inner surface having the first color to the gemstone. The second range of ray directions can correspond to light reflected from the second portion of the inner surface having the second color to the gemstone. The third range of ray directions can correspond to light reflected from the third portion of the inner surface having the third color to the gemstone. The first range of ray directions can be a first range of polar ray directions with respect to a hemispherical reference frame defined by the illumination apparatus. The first range of polar ray directions can include light incident on the gemstone from polar angles of about 45° to about 75° with respect to the hemispherical reference frame. The second range of ray directions can be a second range of polar ray directions with respect to the hemispherical reference frame. The second range of polar ray directions can include light incident on the gemstone from polar angles of about 75° or more with respect to the hemispherical reference frame. The third range of ray directions can be a third range of polar ray directions with respect to the hemispherical reference frame. The third range of polar ray directions can include light incident on the gemstone from polar angles of about 45° or less with respect to the hemispherical reference frame.

The illumination apparatus can further include a light source positioned to illuminate the inner surface of the housing. The light source can be a broadband light source. The light source is a spatially extended light source or a point source.

The illumination apparatus can further include a mounting fixture for positioning the gemstone within the housing. The housing can include an aperture and the imaging device can be positioned relative to the illumination apparatus to acquire the image of the gemstone through the aperture. The aperture can correspond to a polar angle of 90° relative to a hemispherical reference frame defined by the illumination apparatus. The imaging device can be a digital camera.

The imaging device can be positioned between about one centimeter and about 100 centimeters from the gemstone. The imaging device can be positioned between about 20 centimeters and about 30 centimeters from the gemstone, such as about 25 centimeters from the gemstone.

In general, in another aspect, the invention features an apparatus, including a housing having a first portion, a second portion, and a third portion configured to illuminate a first location within the housing with light from a first, second, and third range of ray directions, respectively, wherein light from the first, second, and third ray directions have a first, a second, and a third color, respectively, the first, second, and third colors being different, and a mounting structure configured to position a gemstone at the first location.

Embodiments of the apparatus can include one or more of the following features and/or features of other aspects.

The first, second, and third portions can reflect light of the first, second, and third colors respectively. The first, second, and third portions can transmit light of the first, second, and third colors, respectively. The first, second, and third colors can be complimentary colors. The first, second, and third colors can be red, green, and blue, respectively. The first range of ray directions can include a first range of polar ray directions with respect to a hemispherical reference frame defined by the housing. The first location can correspond to the origin of the hemispherical reference system. The first range of polar ray directions can include light incident at the first location from polar angles of about 45° to about 75° with respect to the hemispherical reference frame. The second range of ray directions can include a second range of polar ray directions with respect to the hemispherical reference frame. The second range of polar ray directions can include light incident at the first location from polar angles of about 75° or more with respect to the hemispherical reference frame. The third range of ray directions can include a third range of polar ray directions with respect to the hemispherical reference frame. The third range of polar ray directions can include light incident on the gemstone from polar angles of about 45° or less with respect to the hemispherical reference frame.

The first range of ray directions can include a first range of azimuthal ray directions with respect to a hemispherical reference flame defined by the housing. The housing can include additional a fourth portion configured to illuminate the first location with light of a fourth color. The housing can include an aperture from which the first location can be observed. The aperture can correspond to a polar angle of 90° relative to a hemispherical reference frame defined by the housing. The apparatus can include an eyepiece lens configured to allowing viewing of the gemstone at the first location through the aperture. The apparatus can include an imaging device configured to acquire an image of the gemstone at the first location through the aperture. The apparatus can include a beamsplitter positioned between the imaging device and the first location. The first location can correspond to the origin of the hemispherical reference system.

The housing can include a cylindrical surface. A radius and a height of the cylindrical surface can be substantially equal. The housing can include a polygonal surface. The mounting structure can include a transparent substrate configured to contact a surface of the gemstone. The transparent substrate can contact a table of the gemstone.

The apparatus can further include a light source configured to illuminate the first, second, and third portions of the housing. The light source can be a broadband light source. The light source can include one or more light emitting diodes. The light source can be an extended light source. The light source can be a point light source.

In another aspect, the invention can feature a handheld device for observing a gemstone including the foregoing apparatus.

In general, in a further aspect, the invention features a computer-implemented method, including generating a representation corresponding to light a gemstone directs to an observation location in response to illumination, wherein the representation differentiates between light incident on the gemstone from at least two different ray directions, and evaluating the gemstone based on light the gemstone directs to the observation location from a first range of ray directions.

Embodiments of the method can include one or more of the following features and/or features of other aspects.

Generating the representation can include providing a data set corresponding to a geometry of the gemstone. The data set corresponding to the geometry of the gemstone can be a CAD file. Providing the data set can include optically scanning the gemstone and generating a stereo-lithographic file based on the optical scanning. Generating the representation can further include tracing paths of light rays through the gemstone using the data set corresponding to the geometry of the gemstone. The traced paths can originate from a source, and a location of the source corresponds to the observation location. The location of the source can correspond to a location between about one centimeter and about 100 centimeters from the gemstone. The location of the source can correspond to a location between about 20 centimeters and about 30 centimeters from the gemstone, such as about 25 centimeters from the gemstone. The path of each light ray exiting the gemstone can be traced to a location on a reference sphere. The path of the light ray can be reverse traced from the location on the reference sphere to a location from which the ray originated.

The representation can correspond to a set of ray directions that the gemstone directs to the observation location. The representation can be a geometrical angular spectrum. The representation can be an integrated geometrical angular spectrum. Evaluating the gemstone can include determining a proportion of ray directions that the gemstone directs to the observation location within the first range of ray directions. The first range of ray directions can correspond to light incident on the gemstone from polar angles from 45° to 75° with respect to a hemispherical reference frame. Evaluating the gemstone can include determining a proportion of ray directions that the gemstone directs to the observation location within a second range of ray directions, wherein the first and second ranges are different. The first range of ray directions can correspond to light incident on the gemstone from polar angles from 75° to 90° with respect to a hemispherical reference frame. Evaluating the gemstone can include determining a proportion of ray directions that the gemstone directs to the observation location within a third range of ray directions, wherein the first, second, and third ranges are different. The first range of ray directions can correspond to light incident on the gemstone from polar angles from 0° to 45° with respect to a hemispherical reference frame. The observation location can be located at 90° with respect to the hemispherical reference frame.

The gemstone can be evaluated based on light the gemstone directs to the observation location from the first range of ray directions at a first wavelength and a second wavelength, wherein the first and second wavelengths are different. The gemstone can be evaluated based on a difference between the light the gemstone directs to the observation location from the first range of ray directions at the first and second wavelengths. The first wavelength can be about 550 nm or less. The second wavelength can be about 550 nm or more. The representation can correspond to an image of the gemstone at the observation location. A first color in the representation can correspond to light directed to the observation location from a first range of ray directions. The first range of ray directions can correspond to light incident on the gemstone from polar angles from 45° to 75° with respect to a hemispherical reference frame. A second color in the representation can correspond to light directed to the observation location from a second range of ray directions, wherein the first and second colors are different and the first and second ranges are different. The second range of ray directions can correspond to light incident on the gemstone from polar angles from 75° to 90° with respect to a hemispherical reference frame A third color in the representation can correspond to light directed to the observation location from a third range of ray directions, wherein the first, second, and third colors are different and the first, second and third second ranges are different. The second range of ray directions can correspond to light incident on the gemstone from polar angles from 0° to 45° with respect to a hemispherical reference frame. The first, second, and third colors can be complimentary colors. The first, second, and third colors can be red, blue, and green.

The method can further include generating additional representations corresponding to light the gemstone directs to the observation location, wherein an orientation of the gemstone with respect to the observation location in each of the representations is different. The gemstone can be evaluated based on variations in light the gemstone directs to the observation location from the first range of ray directions for the different orientations of the gemstone with respect to the observation location. The gemstone can be a diamond. The diamond can be a fancy cut diamond.

In general, in another aspect, the invention features an apparatus for evaluating a gemstone including a memory that stores executable instructions, and a processor that executes the instructions to generate a representation corresponding to light a gemstone directs to an observation location in response to illumination, wherein the representation differentiates between light incident on the gemstone from at least two different ray directions, and evaluate the gemstone based on light the gemstone directs to the observation location from a first range of ray directions.

Embodiments of the apparatus can include one or more features of other aspects.

In general, in another aspect, the invention features an article including a machine-readable medium that stores executable instructions for evaluating a gemstone, the instructions causing a machine to generating a representation corresponding to light a gemstone directs to an observation location in response to illumination, wherein the representation differentiates between light incident on the gemstone from at least two different ray directions, and evaluating the gemstone based on light the gemstone directs to the observation location from a first range of ray directions.

Embodiments of the article can include one or more features of other aspects.

In general, in a further aspect, the invention features a method including generating an angular spectrum for a gemstone and evaluating the gemstone based on a composition of the angular spectrum.

Embodiments of the article can include one or more features of other aspects.

In general, in another aspect, the invention features a method that includes providing a computer file comprising information about cut proportions of a gemstone, tracing paths of rays through the gemstone using the computer file, wherein the rays enter the gemstone through the gemstone crown, determining an intersection of each ray path with the gemstone crown, determining an intersection of each ray path exiting the gemstone with a reference surface, and assigning a grade to the gemstone based on the ray paths.

Embodiments of the article can include one or more of the following features and/or feature of other aspects.

Providing the computer file can include creating the computer file. The computer file can be in STL format, DXF format, or IGES format. The ray paths can be traced using an algorithm executed by a computer. The algorithm can account for Snell's law of refraction for each ray. The algorithm can account for the law of reflection for each ray. The algorithm can account for Fresnel reflections for each ray. The rays can originate from in front of the gemstone's crown. The rays can be directed from in front of the gemstone's crown towards the gemstone's crown. The rays can originate from a side of the gemstone's crown. The rays can be directed from in front of the gemstone's crown towards the gemstone's crown. The reference surface can include a hemispherical surface. The gemstone can be located at the center of the hemispherical surface. The reference surface can include a planar surface. The reference surface can include a spherical surface. The grade can be assigned based on the rays intersection with the crown. The grade can be assigned based on the rays intersection with the reference surface. The grade can be assigned based on the proportion of rays that intersect a portion of the reference surface. The grade can be assigned based on directions of the rays. Rays can be traced for different wavelengths. Rays can be traced for different wavelengths that originate from the same point in the same direction. The grade can be assigned based on a divergence between rays traced for different wavelengths that originate from the same point in the same direction. The rays can be traced for more than one orientation of the gemstone with respect to the reference surface.

The method can further include retracing the rays from the reference surface to their point of origin. The method can further include compiling an image of the gemstone from the traced rays.

In general, in a further aspect, the invention features a method that includes providing an image of a gemstone comprising different colors, wherein the different colors correspond to light incident on the gemstone from different ranges of ray directions, and evaluating the gemstone based on the colors.

Embodiments of the method can include one or more of the following features and/or features of other features.

Providing the image can include illuminating the gemstone with light of different color's from different ray directions, and acquiring the image at an observation location while the gemstone is illuminated. Providing the image can include using a computer to generate a representation corresponding to light the gemstone directs to an observation location in response to illumination, wherein the representation is the image. A first color in the image can correspond to light directed by the gemstone to an observation location from a first range of polar ray directions with respect to a hemispherical reference frame. The first range of polar ray directions can correspond to light incident on the gemstone from polar angles from 45° to 75° with respect to the hemispherical reference frame. A second color in the image can correspond to light directed by the gemstone to the observation location from a second range of polar ray directions with respect to a hemispherical reference frame, wherein the first and second colors can be different and the first and second ranges are different. The second range of polar ray directions can correspond to light incident on the gemstone from polar angles from 75° to 90° with respect to the hemispherical reference frame. A third color in the image can correspond to light directed by the gemstone to the observation location from a third range of polar ray directions with respect to the hemispherical reference frame, wherein the first, second, and third colors are different and the first, second and third second ranges are different. The third range of polar ray directions can correspond to light incident on the gemstone from polar angles from 0° to 45° with respect to the hemispherical reference frame. The first, second, and third colors can be complimentary colors. The first, second, and third colors can be red, blue, and green. Evaluating the gemstone can include determining a proportion of the image comprising the first color. Evaluating the gemstone can further include assigning the gemstone a grade based on the proportion of the image comprising the first color.

The grade can correspond to a brilliance of the gemstone. Evaluating the gemstone can include determining a proportion of the image comprising the second color. Evaluating the gemstone can further include assigning the gemstone a grade based on a proportion of the image comprising the first and second colors. The grade can correspond to a scintillation of the gemstone. Evaluating the gemstone can include determining a proportion of the image comprising the third color. Evaluating the gemstone can further include assigning the gemstone a grade based on a proportion of the image comprising the first and third colors. The grade can correspond to a fire of the gemstone. Evaluating the gemstone can include determining a proportion of the image comprising neither the first, second, or third colors. Evaluating the gemstone can further include assigning the gemstone a grade based on the proportion of the image comprising neither the first, second, or third colors. The grade can correspond to a leakage of the gemstone.

The observation location can be located at 90° with respect to a hemispherical reference frame. The observation location can correspond to a location between about one centimeter and about 100 centimeters from the gemstone. The observation location can correspond to a location between about 20 centimeters and about 30 centimeters from the gemstone, such as about 25 centimeters from the gemstone.

The gemstone can be a diamond. The diamond can be a fancy cut diamond.

In general, in another aspect, the invention features a method that includes determining a proportion of a gemstone that directs light to an observer when illuminated by light from a predetermined subset of illumination directions and assigning a grade to a gemstone based on the determined proportion.

Embodiments of the method can include one or more of the following features and/or features of other aspects.

Assigning the grade can include determining values corresponding to multiple characteristics of the gemstone and deducting from an initial grade based on each value and at least one of the characteristics is related to the portion of the gemstone that directs light to the observer when illuminated by light from the predetermined subset of illumination directions. The proportion of the gemstone that directs light to the observer when illuminated by light from the predetermined subset of illumination directions can be related to a brilliance of the gemstone's appearance. The proportion of the gemstone that directs light to the observer when illuminated by light from the predetermined subset of illumination directions can be related to a contrast of the gemstone's appearance. Assigning the grade can further include determining a value corresponding to a spread of the gemstone and adjusting the grade based on the value. Assigning the grade can further include determining a value corresponding to an amount the gemstone disperses incident illumination and adjusting the initial grade based on the value. Assigning the grade can include adjusting an initial grade based on the proportion of the gemstone that directs light to the observer when illuminated by light from the predetermined subset of illumination directions. The initial grade can be adjusted by deducting from the initial grade based on the proportion of the gemstone that directs light to the observer when illuminated by light from the predetermined subset of illumination directions. The deduction can increase as the proportion decreases.

The predetermined subset of illumination directions can correspond to light incident on the gemstone from polar angles from 45° to 75° with respect to a hemispherical reference frame. The grade can be adjusted based on a proportion of the gemstone that does not direct light to the observer when illuminated from the predetermined subset of illumination directions. The grade can be adjusted by deducting from the initial grade an amount that increases as the proportion of the gemstone that does not direct light to the observer when illuminated from the predetermined subset of illumination directions increases.

Assigning the grade further can include determining a value related to an amount the gemstone disperses incident illumination and adjusting the initial grade based on the value. Assigning the grade can include calculating a value corresponding to an amount the gemstone disperses incident illumination for multiple orientations of the gemstone with respect to the observer and adjusting the initial grade based on the worst value.

The predetermined subset of illumination directions can correspond to light incident on the gemstone from polar angles from 70° or more with respect to a hemispherical reference frame. The predetermined subset of illumination directions can correspond to light incident on the gemstone from polar angles from 75° or more with respect to a hemispherical reference frame. The initial grade can be adjusted based on the weight of the gemstone. Adjusting the initial grade based on the weight of the gemstone can include determining a normalized weight of the gemstone corresponding to the product of the gemstone's weight and a factor related to a dimension of the gemstone. The adjustment based on the weight of the gemstone can account for deviations of the proportions of the gemstone from a gemstone of the same cut having optimal proportions.

The gemstone can be a diamond. The diamond can be a fancy cut diamond. The grade can be assigned based on a cut of the diamond.

Embodiments of the invention may include one or more of the following advantages.

In certain aspects, the invention features reliable, repeatable, objective, and/or inexpensive methods and/or apparatus for evaluating and/or designing diamonds and other gemstones. The methods can be easy to implement.

In some embodiments, the invention features objective techniques for evaluating the quality of a gemstone, such as a diamond, based on its cut. Fancy cut diamonds and brilliant cut diamonds can be evaluated.

The techniques can be implemented using computer programs (e.g., commercially available or custom computer programs). For example, techniques can include ray tracing which can be performed using commercially available optical design programs. As another example, techniques can include image analysis, which can be performed using commercially available image analysis software.

Other features and advantages of the invention will be apparent from the description and drawings, and from the claims.

BRIEF DESCRIPTION OF THE DRAWINGS

FIG. 3A is a cross-sectional view of an embodiment of a mounting structure. FIG. 3B is an exploded perspective view of the mounting structure shown in FIG. 3A. FIG. 3C and FIG. 3D are exploded perspective views of additional embodiments of mounting structures. FIG. 3E is a cross-sectional view of another embodiment of a mounting structure.

FIG. 4A and FIG. 4B are cross sectional and top views, respectively, of the light source and mounting structure. FIG. 4C is a schematic view of a circuit for energizing the light source.

DETAILED DESCRIPTION OF THE PREFERRED EMBODIMENT(S)

The value of a diamond depends on its appearance, which in turn depends on factors intrinsic to the diamond, such as its cut. A diamond's appearance also depends on extrinsic factors, such as how the diamond is illuminated and how it is observed.

Figure 1:
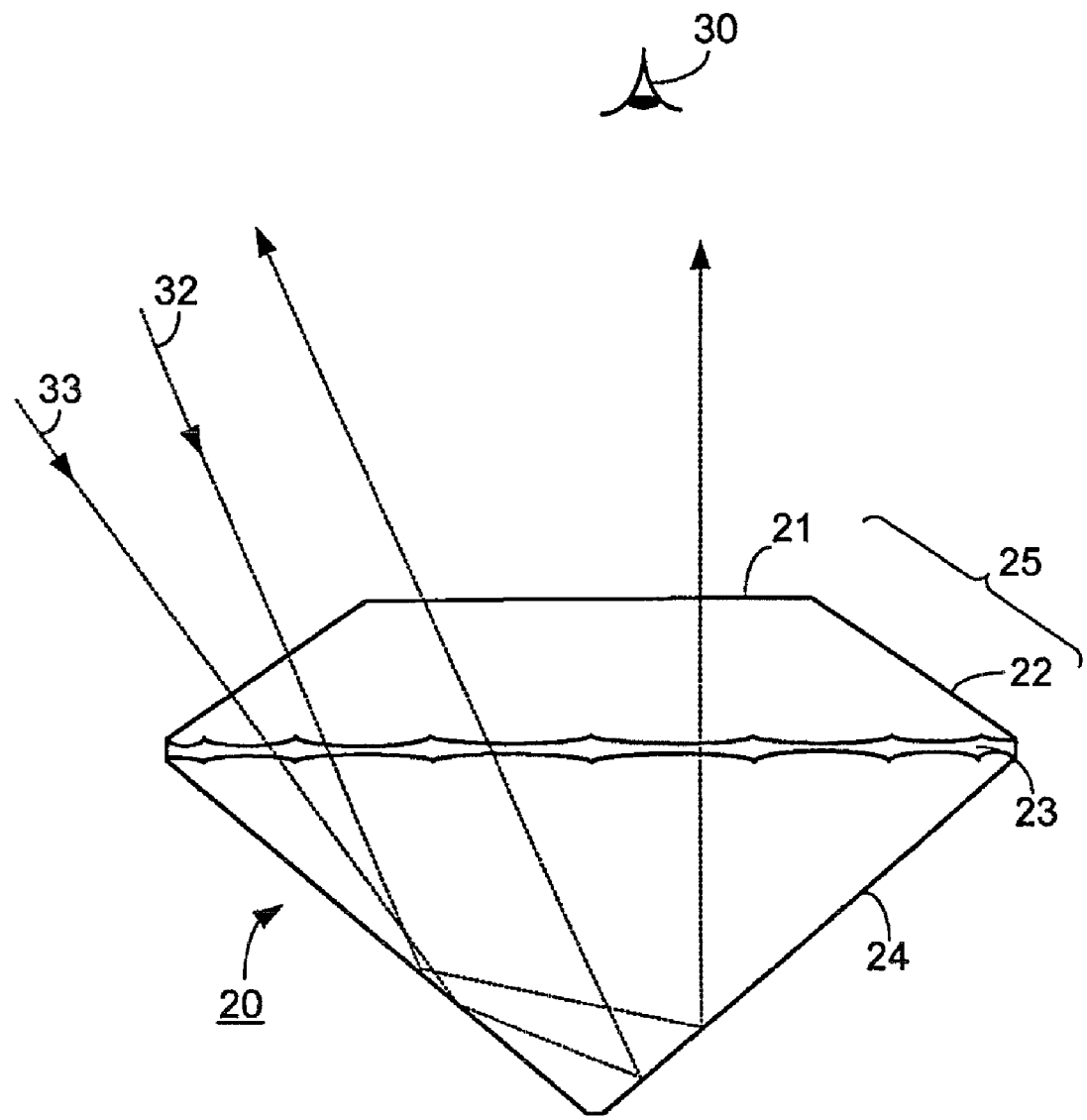
FIG. 1 is a cross-sectional view of a diamond.

Referring to FIG. 1, the cut of a diamond 20 refers to not only the diamond's shape (e.g., diamond 20 is a brilliant round cut diamond), but also to the relative proportion and orientation of the different portions of the diamond, such as the table 21, bezel 22, girdle 23, and pavilion 24. The diamond's crown 25 refers to table 21 and bezel 22. In a typical viewing situation (e.g., where the diamond is facing an observer 30, and observer 30 looks directly along an axis orthogonal to table 21), light (e.g., ray 32 and ray 33) enters diamond 20 through crown 25 and is internally reflected until it is finally refracted and directed to observer 30 (e.g., ray 32) or elsewhere (e.g., ray 33). It is generally undesirable to have light entering or leaking through pavilion 24 or girdle 23 because this can reduce characteristics of a diamond's appearance that make it appealing.

Accordingly, the optical function of diamond's cut includes bringing light from above the crown to an observer's eye. In performing this function, light can be dispersed into its constituent wavelengths and colorful flashes can be observed. This characteristic of a diamond's appearance is known as fire. The optical function of a diamond's cut is also to produce a number of facets that appear bright and others that are left dark, contrasting the bright facets. The number and intensity of the bright facets, and the extent to which their appearance is accentuated by nearby dark facets, is referred to as brilliance, another characteristic of a diamond's appearance. The extent of fire and brilliance observed in a diamond depend on both the diamond's cut proportions and on the illumination conditions under which the diamond is observed. Another characteristic of a diamond's appearance is scintillation, which refers to the diamond's ability to produce an appearance of flashes of light when the diamond, observer, and/or illumination source move relative to each other.

Methods, apparatus, and systems for evaluating a diamond's cut are described herein. The methods include use of metrics related to characteristics of the diamond's appearance, including its brilliance, fire, and/or scintillation, which can allow the diamond's characteristics to be objectively graded.

Figure 2A:
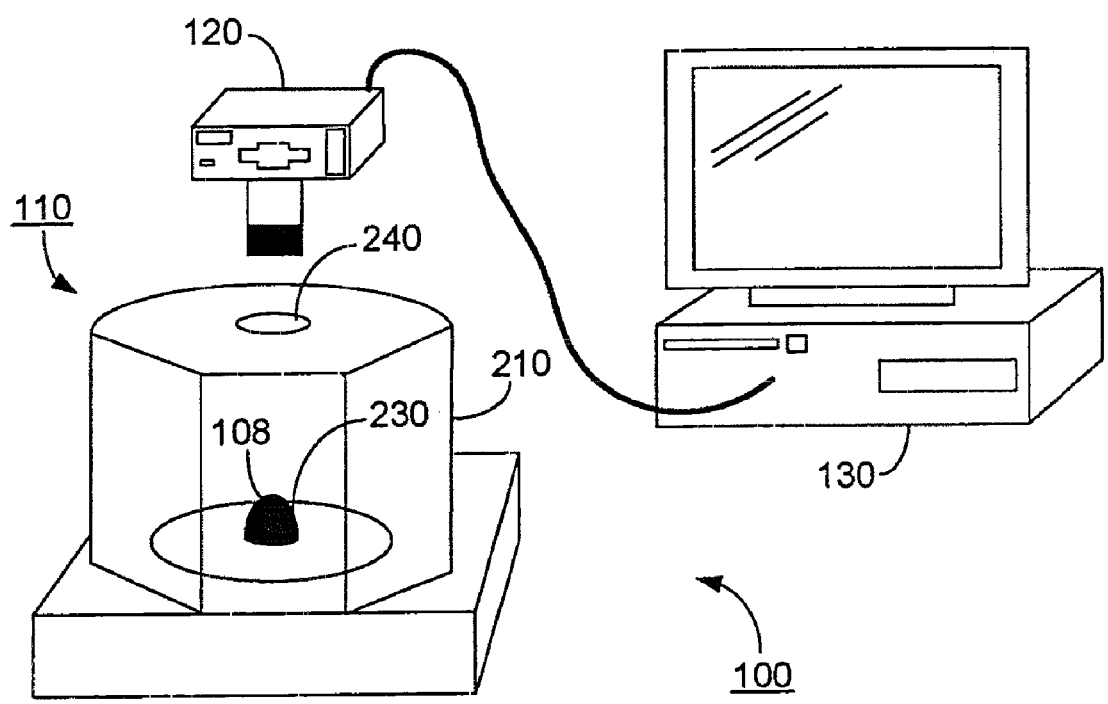
FIG. 2A is a schematic diagram of a system used to evaluate a diamond's cut.

One way to evaluate a diamond's cut is to determine which facets return light to an observer under certain illumination conditions. In other words, the diamond can be evaluated based on which incident light rays are directed towards an observer by each facet. One can make such a determination by illuminating the diamond with light of a different color from each of a number of different ray directions, and seeing which color, if any, each facet directs to an observers. Referring to FIG. 2A, a system 100 is used to provide such illumination conditions, and, subsequently, analyze an image of the diamond acquired under the illumination conditions to evaluate the diamond's cut. System 100 includes an illumination apparatus 110, which illuminates a diamond 101 with multicolored light. An imaging device 120 captures an image of the diamond under the illumination conditions and sends the image to a computer 130.

Figure 2B:
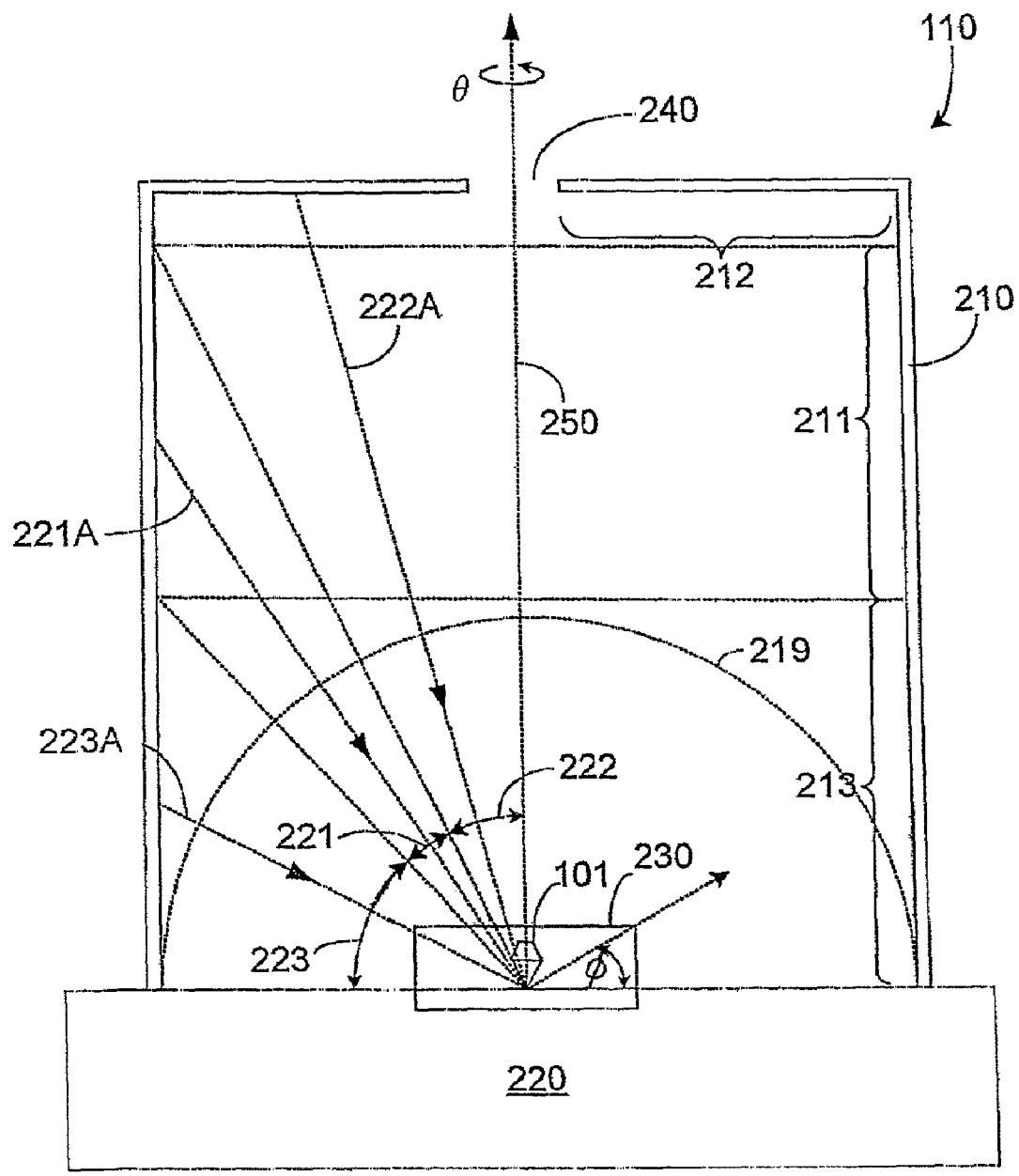
FIG. 2B is a schematic diagram of an illumination apparatus used in the system shown in FIG. 2A.

Referring also to FIG. 2B, illumination apparatus 110 includes a housing 210 and a light source 220. Illumination apparatus 110 also includes an aperture 240 in housing 210, through which imaging device 120 captures images of diamond 101. A mounting fixture 230 positions diamond 101 within housing 210. The mounting fixture positions diamond 101 on an axis 250 with aperture 240.

An inner surface of housing 210 includes three different concentric portions 211, 212, and 213, which are colored red, blue, and green, respectively. During operation, light from light source 220 reflects from the inner surface of housing 210 and illuminates diamond 101. Due to their coloring, portions 211, 212, and 213 illuminate diamond 101 with red, blue, and green light, respectively. Light rays reflected from portion 211 to diamond 101, such as ray 221A, are incident on the diamond within a first range of incident angles 221. Range 221 corresponds to a range of polar angles with respect to a hemispherical reference frame 299 defined by illumination apparatus 110 and centered on diamond 101. Polar angles, $\phi$, are measured from a plane normal to axis 250, and azimuthal angles, $\theta$, are measured within the plane. Light rays reflected from portion 212 to diamond 101 (e.g., ray 222A) are incident on diamond 101 from a second range of polar angles 222, and light rays reflected from portion 213 to diamond 101 (e.g., ray 223A) are incident on diamond 101 from a third range of polar angles 223. Due to the different colors of portions 211, 212, and 213, light incident on diamond 101 is color-coded based on its polar angle of incidence. Diamond 101 directs some of this light along axis 250, through aperture 240, to imaging device 120, which acquires an image of the diamond under these illumination conditions.

In general, polar angle ranges 221-223 can correspond to any three ranges of polar angles in the hemispherical reference frame. In some embodiments, polar angle ranges 221-223 can be selected to correspond to one or more characteristics of a typical viewing environment. For example, range 221 can be selected to correspond to the range of angles from where a diamond receives most of its illumination in a typical viewing environment (e.g., overhead indoor lighting or ambient outdoor lighting). In some embodiments, a lower limit of range 221/upper limit of range 223 can correspond to polar angles of about 20° or more (e.g., about 25° or more, about 30° or more, about 35° or more, about 40° or more, about 45° or more, about 50° or more, about 55° or more, about 60° or more, about 65° or more).

Alternatively, or additionally, range 222 can be selected to correspond to overhead illumination that is occluded by a viewer's head. This range can be selected based on the average size of a viewer's head and/or an average distance from which a viewer typically observes a diamond (e.g., about 10 centimeters or more, about 15 centimeters or more, about 20 centimeters or more, about 25 centimeters or more, about 30 centimeters or more, about 35 centimeters or more, about 40 centimeters or more, about 45 centimeters or more, about 50 centimeters or more). In some embodiments, an upper limit of range 221/lower limit of range 222 can correspond to polar angles of about 85° or less (e.g., about 80° or less, about 75° or less, about 70° or less, about 65° or less, about 60° or less, about 55° or less, about 50° or less, about 45° or less).

An example of polar ranges 221-223 which correspond to illumination in a typical viewing environment that accounts for occlusion due to the viewer's head is as follows: range 221 from about 45° to about 75°; range 222 above about 75°; and range 223 below about 45°. In this example, range 222 corresponds to the occlusion due to a standard head size positioned 25 centimeters from the diamond. A standard head size refers to a head size that is the average of a man's head in the 5th percentile and a woman's head in the 95th percentile, according to the military standard MIL-STD-1472D.

While the inner surface of housing 210 includes three portions of different color's, other embodiments can include different numbers of portions. For example, in general, the inner surface of housing 210 can include two portions, three portions, four portions, five portions, six portions, seven portions, eight portions or more. In general, non-adjacent portions can have the same color or different colors. For example, where a user is interested in studying the diamond's appearance corresponding to illumination from a single range of polar angles, the portion corresponding to those angles can have a first color (e.g., white, red, blue, or green), while the other portions are colored black. Other embodiments are also contemplated. Moreover, in general, the colors are not limited to red, blue, green, white, or black. In general, any combination of colors that can be distinguished in an image of the diamond can be used. In some embodiments, the different colors can be complimentary (e.g., cyan, yellow, and magenta). Colors can be composed of substantially monochromatic spectral content, or can be composed of a band or multiple bands of wavelengths.

Imaging device 120 can be a digital camera, such as a digital camera that includes a CCD array or CMOS array. The distance between imaging device 120 and diamond 101 can vary as desired. Typically, imaging device 120 is positioned between about one centimeter and 100 centimeters from diamond 101. In some embodiments, the distance between imaging device 120 and diamond 101 can correspond to a distance at which a person typically views a diamond, such as between about 20 centimeters and 40 centimeters (e.g., about 25 centimeters).

Imaging device 120 can include passive imaging elements such as one or more lenses or filters. Typically, lenses are used to image diamond 101 onto the sensor of imaging device 120 (e.g., onto a detector array). Lenses can be used, for example, to magnify the image of diamond 101. Filters can be used to reduce extraneous light entering the imaging device and/or to reduce light not corresponding to the red, blue, or green of portions 211-213. In embodiments, the colors of portions 211, 212, and 213 can correspond substantially to the spectral sensitivity of imaging device 120. For example, in embodiments where imaging device utilizes a 24-bit color sensor (e.g., a sensor that uses 8-bit detection for different sensor components each corresponding to a different color), the color of each portion can correspond to a spectral distribution that substantially saturates one of the sensor components. Accordingly, where a sensor component (e.g., a sensor pixel) is exposed to light from one of portions 211-213, it registers a color level of 255 (or close to 255) for one color, and zero (or close to zero) for the other two colors.

In some embodiments, imaging device 120 can include relay optics, which relay the image of the diamond proximate to aperture 240 to a sensor (e.g., a CCD or CMOS array) at a location remote from illumination apparatus 100. Examples of relay optics include free space relay optics (e.g., including mirrors and/or lenses) and waveguiding relay optics such as a bundle of optical fibers.

Computer 130 can be a personal computer. In some embodiments, computer 130 includes an image capture card for receiving images from imaging device 120. Computer 130 can perform an analysis of images of diamond 101, or can output one or more image files (e.g., BMP, TIFF or other format) that can be analyzed using a different computer.

In general, mounting fixture 230 can be any fixture that positions diamond 101 in a desired orientation with respect to housing 210. Typically, mounting fixture 230 positions diamond 101 with the diamond's table orthogonal to axis 250, although, in general, it can be positioned at any angle with respect to axis 250. For example, where diamond's off-axis appearance is to be studied, mounting fixture 230 can be configured to tilt the diamond with respect to axis 250 (i.e., orient the table of diamond 101 at a non-normal angle with respect to axis 250.

Figure 3A:
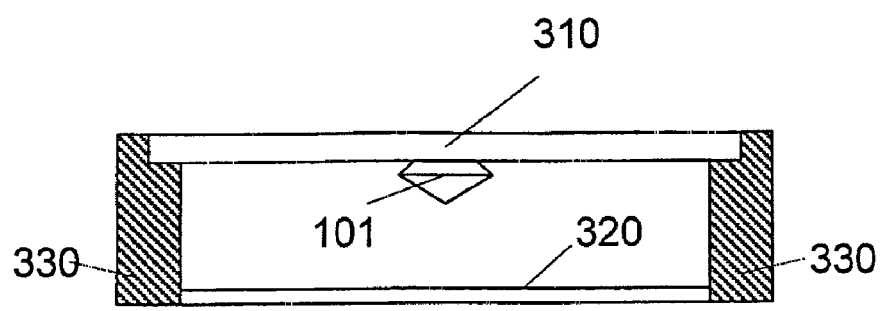
FIGS. 3A-3E are diagrams of embodiments of mounting structures used to position the diamond within the illumination apparatus shown in FIG. 2B. In particular.

In some embodiments, mounting fixture 230 does not include any structure that optically couples to facets of the diamond's pavilion. Optical coupling refers to any structure that changes the optical nature of optical interfaces of a diamond's facets. Structure that optically couples to a facet can change the amount of light reflected at that interface, and can reduce the amount of light that experiences total internal reflection within the pavilion. Accordingly, optical coupling of one or more pavilion facets to the mounting structure can affect the diamond's appearance. Examples of mounting structures are shown in FIG. 3A-3D. In each illustrated embodiment, the mounting structure includes a glass flat 310 (e.g., a microscope slide), a filter 320, and a stage body 330. Stage body 330 includes an aperture 331, which allows the light source (not shown) to illuminate diamond 101 from beneath. Referring specifically to FIG. 3A, diamond 101 is mounted by contacting the table of the diamond to a surface of glass flat 310. Adherence forces (e.g., vacuum forces, electrostatic forces) cause the table to adhere to the glass surface, allowing the mounting structure to suspend diamond 101 above the light source (not shown) when glass flat 310 is rested on stage body 330. Filter 320 sits within stage body 330, and filters the light illuminating diamond 101 from beneath. Filter 320 can be used when acquiring photographs of diamond 101 using apparatus 110 to provide a specific color background (e.g., a white background). In addition, when filter 320 used, light leaked by diamond 101 appears the color of the filter in an image. Filter 320 can be frosted to diffuse illumination from the light source. In some embodiments, one or both surfaces of filter 320 can be curved (e.g., concave or convex with respect to diamond 101.

Figures 3B, 3C, 3D:
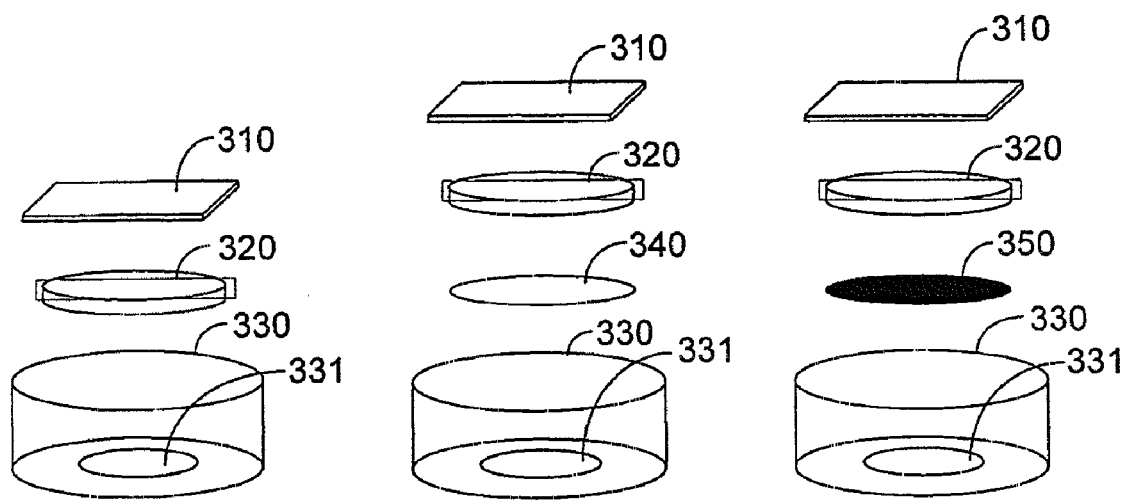

Referring to FIG. 3C, in some embodiments, the mounting structure can include one or more additional passive optical components, such as a white filter 340. White filter 340 can reduce the brightness of the light source outside the diamond's border in an image of diamond 101. White filter 340 may be included, for example, when studying leakage in diamond 101, as the reduced brightness can enhance the appearance of leaked light in an image of diamond 101.

In some embodiments, it may be desirable to block light that illuminates the diamond from behind. For example, referring to FIG. 3D, where a user wants to illuminate the diamond exclusively by colored light from the inner surface of housing 210, they may block aperture 331 using a light block 350. Light block 350 can enhance the appearance of colored light in an image of diamond 101. Leaked light appears black in an image of diamond 101 when using light block 350.

Figure 3E:
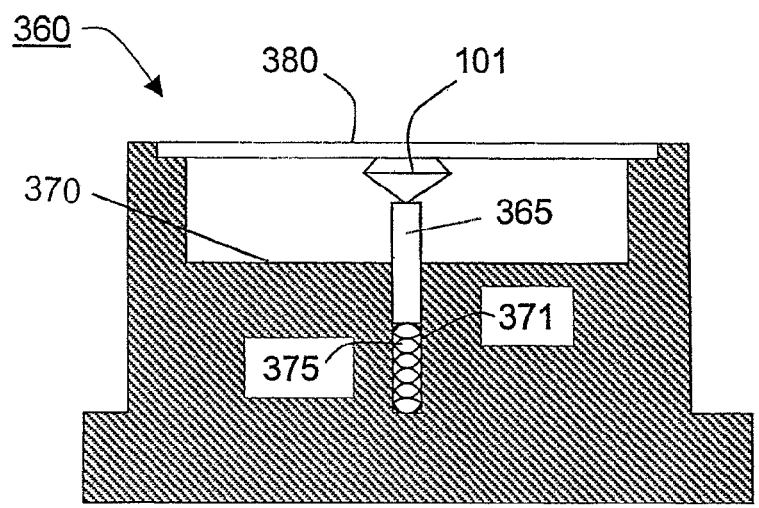

In some embodiments, a mounting fixture can include one or more additional elements that support diamond 101 from underneath. For example, referring to FIG. 3E, a mounting fixture 360 includes a support post 365, which supports diamond 101 from beneath the diamond's pavilion. Mounting fixture 360 also includes a base 370, which includes a shaft 371, into which support post 365 is placed. A spring 375 applies an upward force on diamond 101, pressing it against a glass flat 380 that rests on base 370. Spring 375 also allows support post 365 to travel up and down, accommodating diamonds of different size. The diameter of shaft 371 and support post 365 are closely matched, preventing support post 365 from tilting significantly to one side.

Referring again to FIGS. 2A and 2B, in general, light source 220 should include sufficient intensity at wavelengths corresponding to the red, blue, and green of portions 211, 212, and 213, respectively, to adequately illuminate the diamond with red, blue, and green light. Adequate illumination provides sufficient intensity so that the different colors are identifiable in an image acquired by imaging device 120. Light source 220 can include both active and passive optical elements. Active optical elements emit light (e.g., a light bulb or laser). Passive optical elements change one or more properties of the light emitted from an active optical element (e.g., filter the light, diffuse the light). In some embodiments, light source 220 can include a broadband active optical element (e.g., including light from all wavelengths within a band of wavelengths from about 400 nm to about 700 nm). Examples of broadband active optical elements include white-light light emitting diodes (LEDs), incandescent bulbs, and fluorescent bulbs. In some embodiments, light can be guided from a source to housing 210 using a waveguide, such as an optical fiber or a wedge light guide.

Light source 220 can be a spatially extended source. A spatially extended source can include, for example, several discrete optical elements positioned over an extended area (e.g., multiple LEDs), or a single active optical element that extends over an area (e.g., a fluorescent bulb tube). In some embodiments, the source can extend over an area of about 10 $cm^2$ or more (e.g., about 20 $cm^2$ or more, about 30 $cm^2$ or more, about 40 $cm^2$ or more, about 50 $cm^2$ or more). Optionally, the light source can include one or more passive optical elements that homogenize, filter, or otherwise interact with the light emitted from the active element (e.g., bulb) in the light source. For example, light source 220 can include one or more diffusing sheets, which homogenize light from the active element entering housing 210.

Figure 4A:
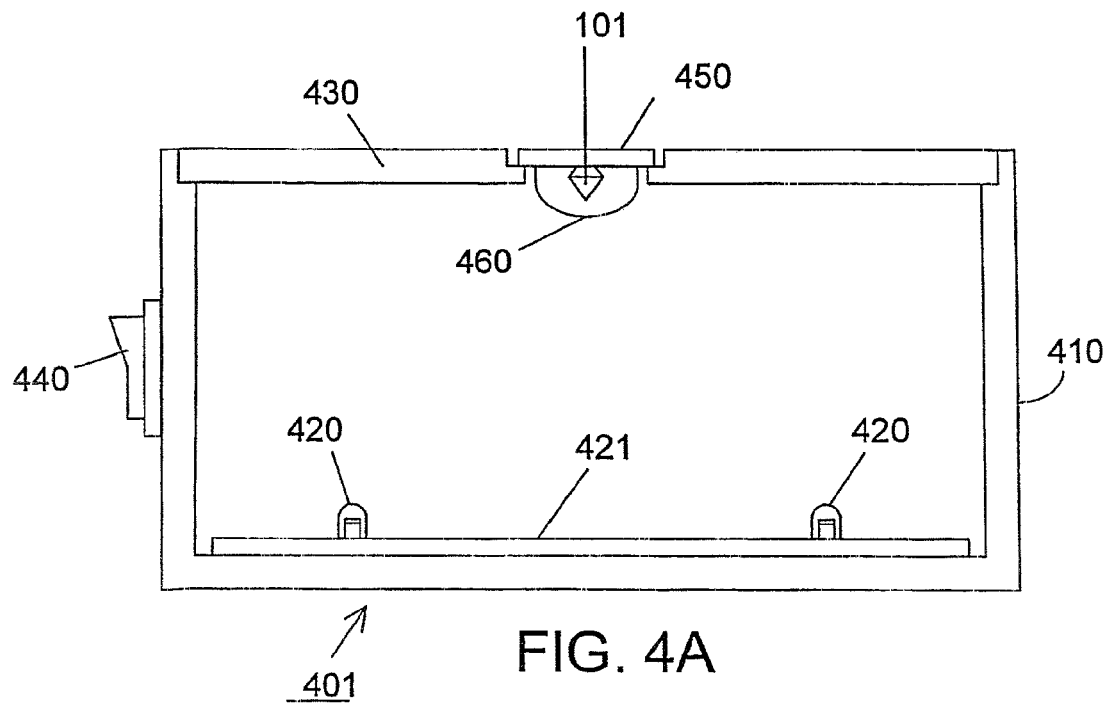
FIGS. 4A-4C are diagrams of an embodiment of a light source and mounting structure for an illumination apparatus. In particular.
Figure 4B:
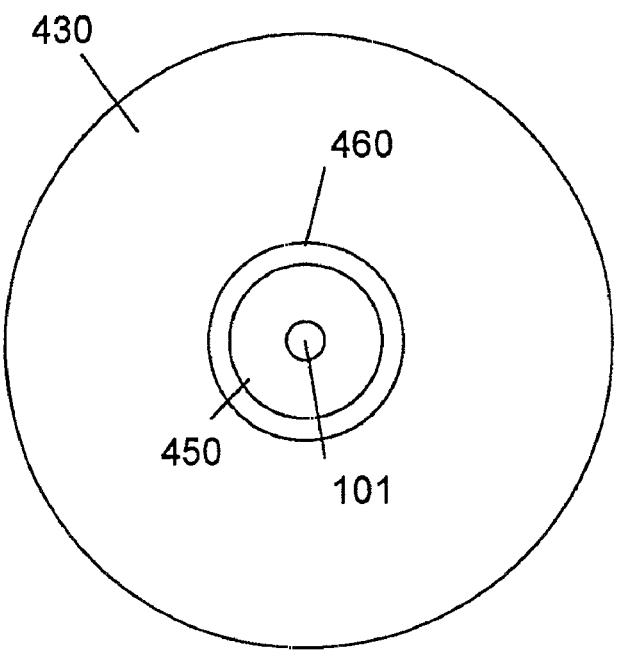
Figure 4C:
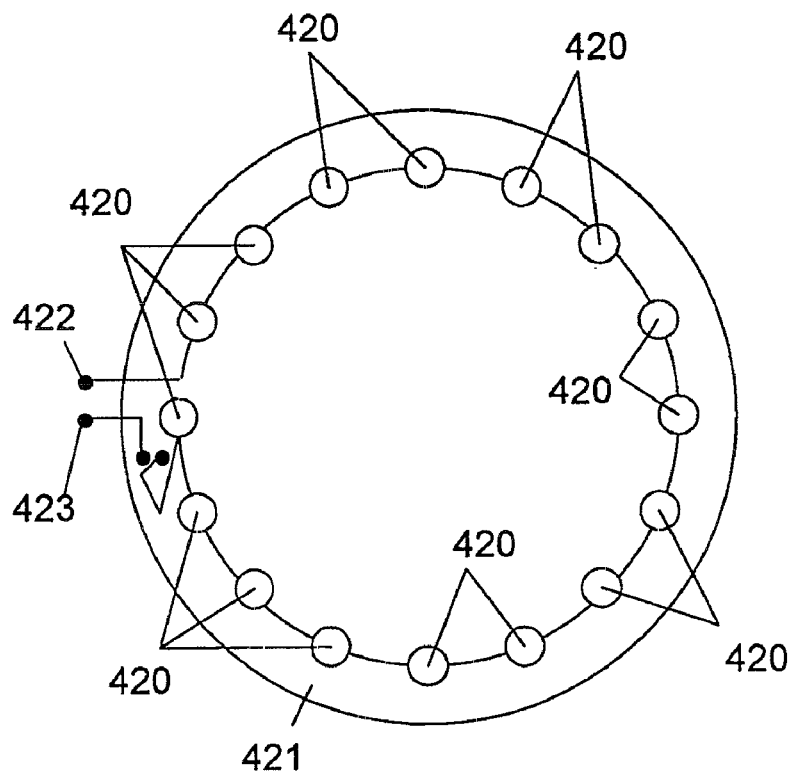

Referring to FIGS. 4A-4C, an example of a spatially extended source is light source 401, which includes multiple LEDs 420 (e.g., white, red, green, and/or blue LEDs) arranged to illuminate a housing (not shown) through a diffuse light filter 430 (e.g., a sheet of frosted glass, or a light scattering polymer sheet). Diffuse light filter 430 homogenizes light emitted from LEDs 420, providing the housing with substantially diffuse, homogeneous illumination. LEDs 420 are attached to a board 421, which is placed in a base 410. LEDs 420 are turned on and off by means of a toggle switch 440. Diffuse light filter 430 sits on base 410. A cup 460 is positioned in an aperture at the center of diffuse light filter 430, creating a cavity into which diamond 101 can be positioned. Cup 460 can be clear, diffusely transmissive, or opaque. Diamond 101 adheres to a clear glass flat 450, which covers the cavity. Adjusting the position of glass flat 450 relative to diffuse light filter 430 changes the position of diamond 101, allowing a user to optimally position diamond 101 relative to light source 401 and the housing.\

Referring specifically to FIG. 4C, which shows a wiring schematic for LEDs 420, in some embodiments, the LEDs are connected in parallel. LEDs 420 are connected to a power source (e.g., an AC power source, such as a mains connection, or a DC power source, such as a battery) via terminals 422 and 423.

In certain embodiments, illumination apparatus 110 can utilize ambient illumination, such as overhead illumination (such as typically used in a work or domestic environment), or sunlight (e.g., direct or indirect sunlight). Illumination apparatus can direct ambient illumination into housing 210 by including one or more light directing elements (e.g., one or more minors) beneath housing 210. Alternatively, or additionally, in some embodiments, housing 210 can include a transparent material which filters out part of the ambient illumination incident on the outside of housing 210, while transmitting some of the ambient illumination so that portions 211-213 transmit the appropriate color light to diamond 101. Transparent materials include polymer's (e.g., plastics) and/or glasses that can include components (e.g., dyes) that absorb or reflect wavelengths of light not contributing to the appropriate color. In some embodiments that utilize ambient illumination, illumination apparatus 110 need not include light source 220.

In general, an illumination apparatus can include additional or fewer components to those shown for illumination apparatus 110. For example, in some embodiments, an illumination apparatus can be configured so that an observer can directly observe diamond 101 instead of or in addition to acquiring an image of diamond 101 with imaging device 120. Where diamond 101 is to be observed directly, imaging device 120 can be replaced by an eyepiece lens at aperture 240, to provide a magnified image of the diamond to the observer. In some embodiments, illumination apparatus 110 can include a beam splitter at aperture 240, which directs part of the light from diamond 101 at aperture 240 to imaging device 120 and part of the light to an eyepiece lens, for example.

Figure 5A:
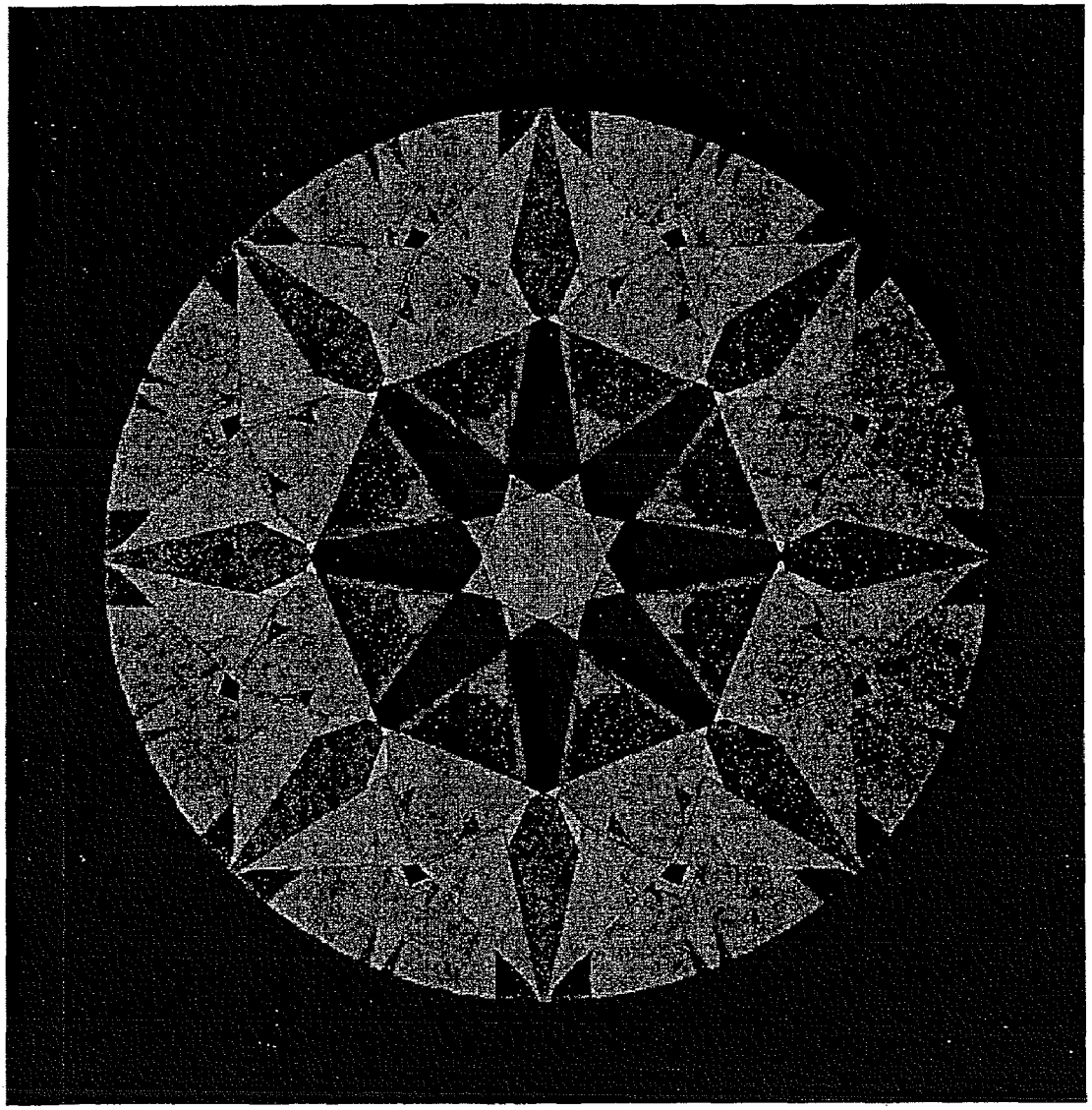
FIG. 5A is an example of a color-coded image of a diamond.

An example of an image of a diamond acquired using system 100 is shown in FIG. 5A. The portions that include a red component correspond to facets of a diamond that direct light from range 221 to an observer. Similarly, portions that include a blue component and a green component correspond to facets of the diamond that direct light from ranges 222 and 223 to the observer, respectively. Accordingly, the image is color-coded to provide information about which facets direct illumination from different illumination ranges to an observer. Where a color in the image corresponds to a range of ray directions which illuminate the diamond under typical viewing conditions, the facets that include that color should appear bright under those illumination conditions. For example, the red portions in the image in FIG. 5A correspond to illumination incident on the diamond with polar ray directions from about 45° to about 75°. These directions correspond to the directions from which the diamond is usually illuminated, so these portions should appear bright under typical viewing conditions.

Furthermore, where a color in the image corresponds to a range of ray directions that are typically obscured, the facets that appear that color in the image should appear dark under typical viewing conditions. For example, the blue portions in the image in FIG. 5A correspond to illumination incident on the diamond with polar ray directions of about 75° and greater. Rays from these directions are usually obscured by an observer's head, so these portions should appear dark when viewed under typical viewing conditions. Similarly, the green portions of the image in FIG. 5A correspond to rays having low angles of incidence (i.e., less than 45°), which do not typically provide much illumination intensity under typical viewing conditions. Accordingly, these portions should also appear dark under typical viewing conditions. However, when an observer views the diamond at an angle, instead of from directly above the table, overhead illumination which corresponded to the 45° to 75° range when viewed from above will be incident on the diamond at a lower angle, and at least some of the green portions should appear bright. Accordingly, the color corresponding to range 223 may appear bright or dark depending on the orientation of the diamond, observer and illumination, and may appear to sparkle as the diamond, observer, and/or illumination move relative to each other.

Figure 5B:
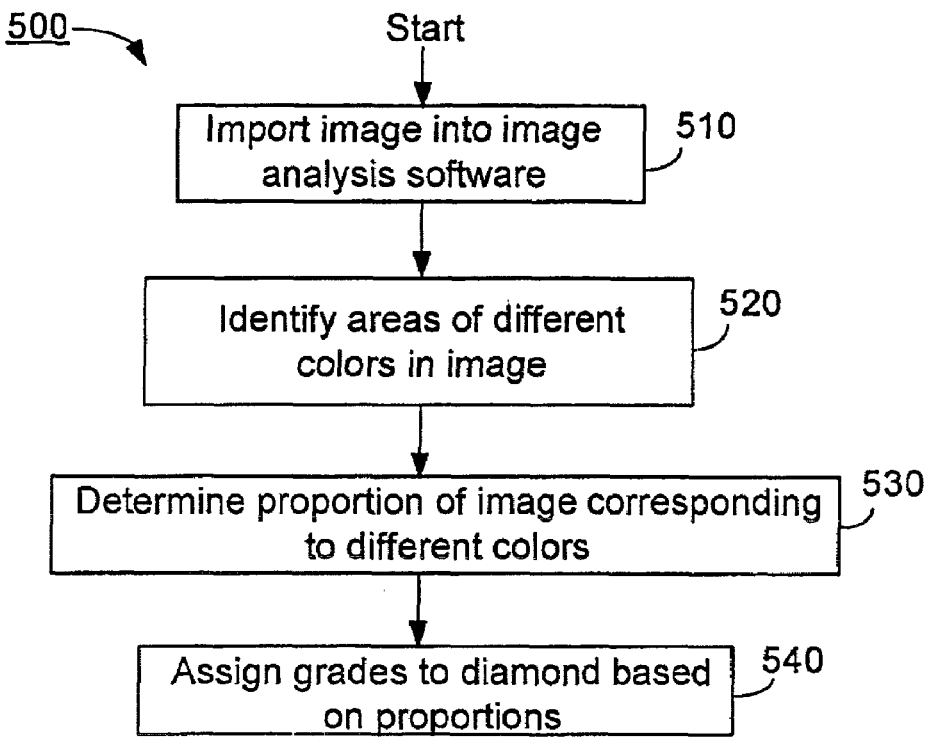
FIG. 5B is a flow chart summarizing steps in a process used to evaluate a color-coded image of a diamond.

Referring to FIG. 5B, once a color-coded image has been acquired, it can be analyzed to evaluate the diamond. Flow chart 500 shows a computer-implemented process which can be used to analyze a color-coded image, and evaluate the diamond according to the image. First, the image is imported into an image analysis program (step 510). Image analysis programs, such as ImageJ (available online at the website "http://rsb.info.nih.gov/ij/") or custom developed code, may be used. Once the image has been imported, the program identifies the area of the image corresponding to the diamond and then identifies areas of different color (e.g., red, blue, green, black) in the image (step 520). Either or both of these tasks can be performed automatically, or with input from the user to ensure that the edge of the diamond and the boundaries of portions of different color are accurately identified.

Next, the program determines the proportion of the image composed of each of the different colors (step 530). Typically, for each color, this involves binning the number of pixels of each image that contain that color. The total number of pixels containing a color can be expressed as a raw number and/or as a percentage or fraction of the diamond image. Additional information can also be obtained, such as the number of pixels containing no color (e.g., black pixels) and/or the number of pixels containing more than one color.\

Finally, the program can assign grades to one or more characteristics of the diamond based on the proportions of the different colors in diamond image (step 540). In some embodiments, a grade can correspond to a proportion of one of the colors in the image. As an example, a grade can be assigned that corresponds to the proportion of red in the image. Where red corresponds to overhead illumination that is not obscured under typical viewing conditions (e.g., from about 45° to about 75°), this grade corresponds to the area of the diamond that appears bright under typical viewing conditions and is related to the brightness of the diamond. If the image includes a relatively high percentage of reds (e.g., about 35% or more, about 40% or more, about 45% or more, about 50% or more, about 55% or more, about 60% or more, about 65% or more, about 70% or more, about 75% or more), the diamond can receive a relatively high grade for brightness. Alternatively, where the image includes a relatively low percentage of reds (e.g., about 35% or less, about 30% or less, about 25% or less, about 20% or less, about 15% or less, about 10% or less), the diamond can receive a relatively low grade for brightness.

As another example, a grade can be assigned that corresponds to the proportion of blue in the image. Where blue corresponds to overhead illumination that is obscured under typical viewing conditions (e.g., greater than about 75°), this grade corresponds to the area of the diamond that appears dark under typical viewing conditions and is related to the contrast of the diamond. Typically, at least some dark facets are desirable for a diamond's appearance because they accentuate the bright facets. Moreover, as a viewer moves their head relative to the diamond and/or illumination, at least some of these facets can appear bright, contributing to scintillation in the diamond. However, if a substantial area of the diamond is dark, it can appear dull. Accordingly, if the image includes a relatively high percentage of blues (e.g., about 20% or more, about 25% or more, about 30% or more, about 35% or more, about 40% or more, about 50% or more, about 60% or more) or a relatively low percentage of blues (e.g., about 15% or less, about 12% or less, about 10% or less, about 8% or less, about 7% or less, about 6% or less, about 5% or less, about 4% or less, about 3% or less, about 2% or less), the diamond can receive a relatively low grade for contrast. Alternatively, where the amount of blue is in an intermediate range (e.g., between about 10% and about 40%), the diamond can receive a relatively high grade for contrast.

In some embodiments, a grade can correspond to a proportion of two of the colors in the image. For example, the diamond can be assigned a grade based on the proportion of green and red in the image. Where red corresponds to overhead illumination that is not obscured under typical viewing conditions (e.g., from about 45° to about 75°), and green corresponds to angles which don't provide significant illumination under typical viewing conditions (e.g., less than about 45°), this grade corresponds to a proportion of the diamond that can contribute to scintillation in the diamond under typical viewing conditions. If the image includes a relatively high percentage of reds and greens (e.g., about 40% or more, about 45% or more, about 50% or more, about 55% or more, about 60% or more, about 65% or more, about 70% or more, about 75% or more, about 80% or more), the diamond can receive a relatively high grade for scintillation. Alternatively, where the image includes a relatively low percentage of reds and greens (e.g., about 40% or less, about 35% or less, about 30% or less, about 25% or less, about 20% or less, about 15% or less, about 10% or less), the diamond can receive a relatively low grade for scintillation.

In another example, the diamond can be assigned a grade based on the proportion of red and blue in the image. Where red corresponds to overhead illumination that is not obscured under typical viewing conditions (e.g., from about 45° to about 75°), and blue corresponds to typically obscured rays (e.g., greater than about 75°), this grade corresponds to a proportion of the diamond that appears bright or accentuates the bright portions by providing contrast under typical viewing conditions. In other words, the amount of red and blue in the image is related to the diamond's brilliance. If the image includes a relatively high percentage of reds and blues (e.g., about 40% or more, about 45% or more, about 50% or more, about 55% or more, about 60% or more, about 65% or more, about 70% or more, about 75% or more, about 80% or more), the diamond can receive a relatively high grade for brilliance. Alternatively, where the image includes a relatively low percentage of reds and blues (e.g., about 40% or less, about 35% or less, about 30% or less, about 25% or less, about 20% or less, about 15% or less, about 10% or less), the diamond can receive a relatively low grade for brilliance.

In some embodiments, the diamond can be assigned a grade based on the proportion and/or distribution of red, blue, and green in the image. Correspondingly, the diamond can be assigned a grade based on the proportion of the image that is not red, blue, or green. The portions of the image that are not red, blue, or green can appear black or white depending on the illumination conditions. For example, where light from the light source illuminates the diamond from behind (e.g., through the pavilion), portions of the image may appear white. Alternatively, where the light source is blocked behind the diamond, these portions should appeal black. Portions of the image that are neither red, blue, nor green correspond to facets that do not typically bring light to an observer under typical illumination conditions, and correspond to light leakage. Accordingly, where the image includes a relatively high percentage of reds, blues, and greens (e.g., about 50% or more, about 55% or more, about 60% or more, about 65% or more, about 70% or more, about 75% or more, about 80% or more, about 85% or more, about 90% or more), the diamond can receive a relatively high grade for leakage. Alternatively, where the image includes a low percentage of reds and blues (e.g., about 50% or less, about 45% or less, about 40% or less, about 35% or less, about 30% or less, about 25% or less, about 20% or less, about 15% or less, about 10% or less), the diamond can receive a relatively low leakage grade.

In general, the relative percentage that corresponds to a good and/or bad grade for a characteristic of the gemstone can vary. In some embodiments, a grading scale can be assigned empirically, for example, by a professional diamond laboratory, such as the laboratory of the American Gem Society (Las Vegas, Nev.). The grading scale for each characteristic can vary depending on one or more factors, such as the cut of the gemstone and/or the weight of the gemstone. Examples of grading schemes are discussed below.

Figure 5C:
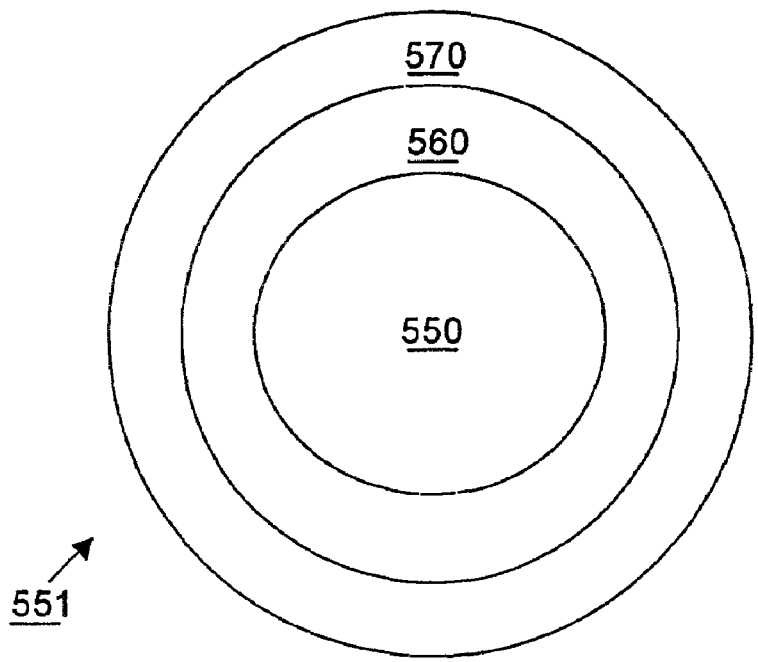
FIG. 5C is a diagram showing different portions of a color-coded image of a diamond

A color-coded image of a diamond can also be analyzed by studying the amount of each color in zones of the image corresponding to different regions of the diamond. For example, referring to FIG. 5C, in some embodiments, a diamond image 551 is differentiated into three zones: a table 550, an inner bezel 560, and an outer bezel 570, corresponding to the inner third, middle third, and outer third of the diamond's area in the image. The amount of color in each portion can be separately determined, allowing the diamond's appearance in different regions to be evaluated. In embodiments, a diamond's image can be separated into less than or more than three zones (e.g., two, four, five, six, or more zones). The zones can correspond to annular zones, such as shown in FIG. 5C, or can be other zones (e.g., segmented zones).

While the color-coded image shown in FIG. 5A was acquired with diamond's table orthogonal to axis 250, in general, color-coded images can be acquired with the diamond at any orientation with respect to axis 250. In some embodiments, color-coded images can be acquired for a diamond at multiple orientations with respect to axis 250. For example, images can be acquired with the table normal tilted by about 1° or more with respected to axis 25 (e.g., about 2° or more, about 3° or more, about 4° or more, about 5° or more, about 8° or more, about 10° or more, about 12° or more, about 15° or more, about 20° or more, about 25° or more, about 30° or more).

In some embodiments, a series of images of a diamond at different orientations with respect to axis 250 can be acquired Variations between the images can be analyzed to evaluate the diamond's appearance under dynamic conditions (e.g., during relative motion between the observer, illumination, and diamond). For example, changes in the brilliance of a diamond at different orientations with respect to an observer are related to scintillation. Accordingly, where an amount of a color in images of a diamond acquired with the diamond at different orientations varies significantly, the diamond can be assigned a high grade for scintillation. For example, for a particular variation in the diamond's orientation, where the percentage of green varies by about 20% or more (e.g., about 30% or more, about 40% or more, about 50% or more, about 60% or more, about 70% or more) between images of a diamond acquired at different orientations, the diamond can receive a grade for scintillation. Of course, for smaller changes in orientation, the percentage variation of green corresponding to a relatively high grade for scintillation can be smaller. For the particular orientation change, if the percentage of greens varies by about 20% or less (e.g., about 15% or less, about 10% or less, about 5% or less), the diamond can receive relatively low grade for scintillation. Variations in the distribution of a color between images of a diamond acquired at different orientations with respect to axis 250 can also be used to evaluate the diamond's appearance. In some embodiments, variations in the distribution of green between different images can be related to scintillation. For example, where one facet is green in a first orientation, and black in a second orientation, and a different facet is black and green in the first and second orientations, the distribution of green changes between the images, while the percentage of green is approximately constant. Despite the percentage of green staying approximately constant, the diamond can appear to sparkle to an observer, due to the different facets changing from bright to dark and vice-versa. Accordingly, where significant redistribution of color occurs between images of a diamond acquired at different orientations, the diamond can receive a high grade for scintillation. For example, for a particular change in the diamond's orientation, where the distribution of green changes by about 10% or more (e.g., about 15% or more, about 20% or more, about 25% or more, about 30% or more, about 40% or more, about 50% or more), the diamond can receive a relatively high grade for scintillation. Where the distribution of green varies by about 10% or less (e.g., about 8% or less, about 5% or less), the diamond can receive relatively low grade for scintillation.

Furthermore, in some embodiments, a diamond may be evaluated by acquiring images of the diamond for multiple different configurations of the inner surface of housing 210.

As an example, consider a configuration where the inner surface of housing 210 includes only two portions: a white portion corresponding to polar ray directions from 0° to α, and a black portion extending from α to the polar ray direction corresponding to aperture 240. Images of the diamond can be acquired for decreasing values of α until the image displays a predetermined threshold proportion of black, corresponding to a desirable amount of contrast in the diamond's appearance. This value of α provides a measure of how occlusion due to a viewer will impact the diamond's appearance.

Moreover, while portions 211-213 are concentric portions, in some embodiments, housing 210 can include portions that are not concentric. For example, housing 210 can include colors that change as a function of azimuthal angle. Illuminating a diamond with azimuthally asymmetric illumination can be used to evaluate diamonds that are asymmetric (e.g., fancy cut diamonds such as oval or marquise diamonds or rectangular princess cut diamonds).

In some embodiments, housing 210 can include portions that extend over relatively small polar and azimuthal angular ranges (e.g., about 20° or less, about 10° or less, about 5° or less). For example, in certain embodiments, housing 210 can include one or more relatively small portions (e.g., circular portions or rectangular portions) which reflect white light. Such portions illuminate the diamond with white light over a relatively narrow range of angles. Dispersion of the white light by the diamond can give rise to different facets having different hues as viewed at the imaging device. As dispersion is related to the diamond's fire, such illumination can provide images related to fire.

While housing 210 has an octagonal shape, in general, housings can have other shapes as well. For example, housings can have polygonal (e.g., regular or irregular polygons) or cylindrical shapes. Examples of polygons include rectangles, squares, pentagons, hexagons, heptagons, decagons, as well as polygons with more than 10 sides. In some embodiments, a housing can include both curved and planar surfaces. For example, a housing can include opposing sides that are semicircular in shape, that are adjacent to a pair of opposing planar sides. In certain embodiments, a housing can be hemispherical or in the shape of a beehive.

Figure 6A:
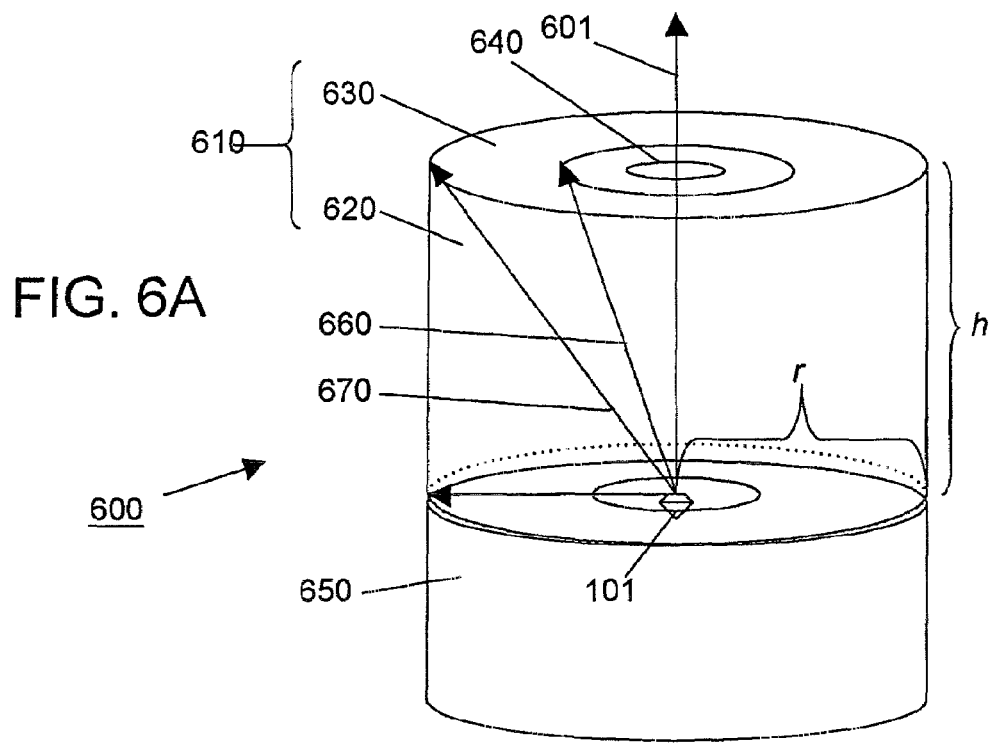
FIGS. 6A and 6B are a perspective and cross-sectional view of another embodiment of an illumination apparatus.
Figure 6B:
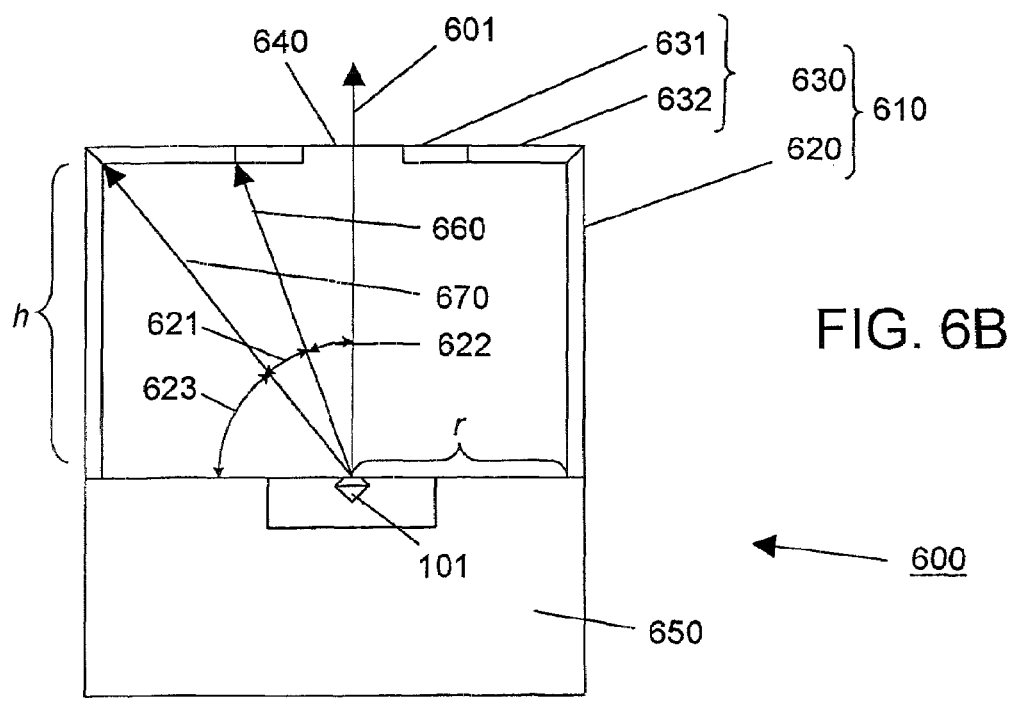

Referring to FIGS. 6A and 6B, an example of a housing with a cylindrical shape is housing 610 of illumination apparatus 600. Housing 610 is composed of a cylindrical wall 620 and a circular cover 630. An aperture 631 in cover 630 provides a line of sight to diamond 101 along an axis 601. Illumination apparatus 600 also includes a light source 650, which can include, for example, a number of LEDs (see, e.g., FIGS. 4A-4C). Light source 650 illuminates the inner surface of housing 610, which reflects light from light source 650 towards diamond 101. Cover 630 includes two concentric portions 631 and 632, the inner surfaces of which reflect different colors toward diamond 101. Light reflected from portion 631 towards diamond 101 corresponds to a range 622 of polar ray angles, while light reflected from portion 632 corresponds to a range 621 of polar ray angles. The inner surface of cylindrical wall 620 reflects a third color, different from the colors reflected by portions 631 and 632, towards diamond 101. The inner surface of cylindrical wall 620 directs light towards diamond 101 along a range 623 of polar ray angle directions.

In housing 610, the ratio of the height, h, of cylindrical wall 620 to its radius, r, is selected so that range 623 of polar ray angles is a particular amount. For example, where illumination of the third color along polar ray directions from 0° to 45° are desired, h can be selected so that h=r. More generally, the ratio of h to r can vary as desired. In some embodiments, the ratio of h to r can be chosen so that cover 630 includes only a single portion which provides light of one color along a particular range of polar ray directions, while cylindrical wall 620 is composed of multiple differently colored portions. In certain embodiments, both cover 630 and cylindrical wall 620 can include differently colored portions. Note, that height, h, and radius, r, correspond to the inner surface dimensions of housing 610.

In general, the size and form factor of the illumination apparatus can vary as desired. For example, as shown in FIG. 2A, in some embodiments, an illumination apparatus can be in the form of a tabletop apparatus. In some embodiments, an illumination apparatus can be a handheld apparatus. A handheld illumination apparatus can include an internal light source, such as an array of LEDs (e.g., see FIG. 3E) or can utilize ambient light (e.g., overhead room light or sunlight).

Figure 7A:
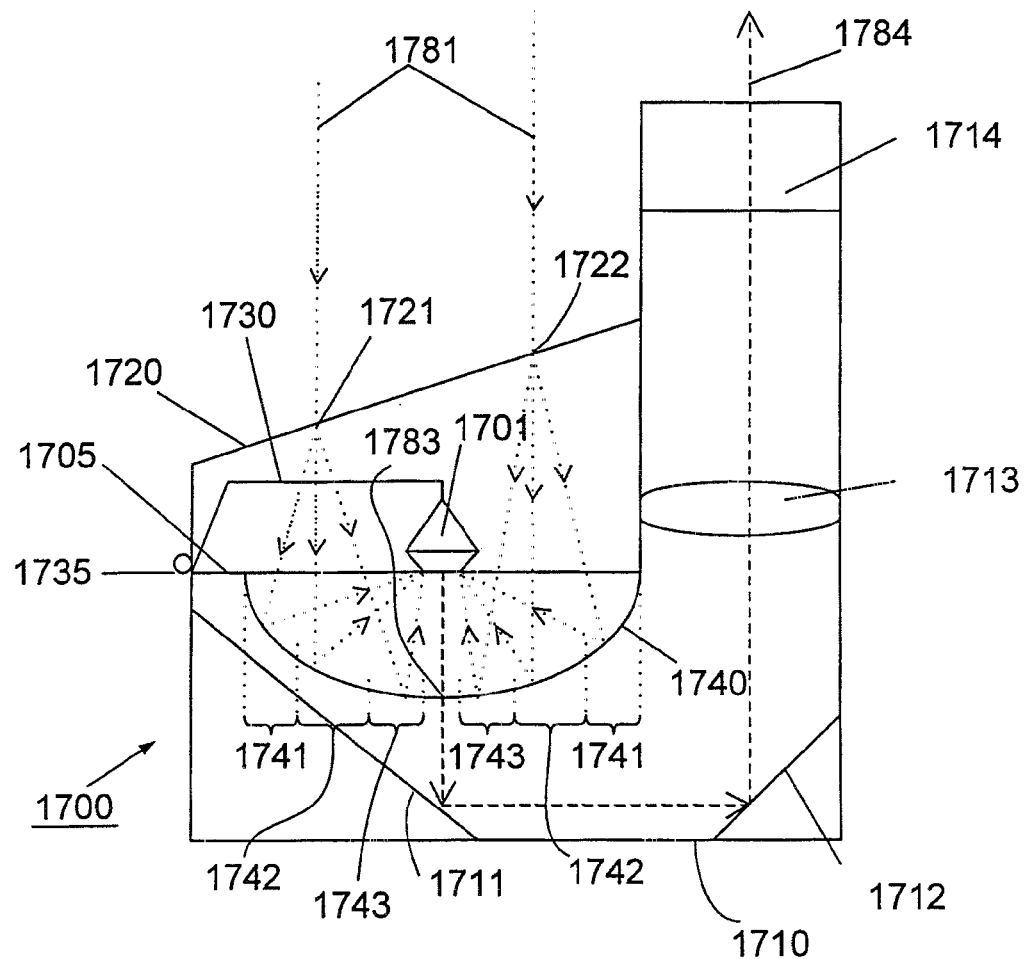
FIG. 7A is a diagram of an embodiment of an illumination apparatus for evaluating a diamond.

Referring to FIG. 7A, another embodiment of an illumination apparatus 1700 includes a base 1710 with a reflecting surface 1740 of different colors that reflects ambient illumination to illuminate a diamond 1701 with light of different colors from different directions. A stylus 1730 holds diamond 1701 against a transparent gemstone stage 1705 (e.g., a glass stage). Stylus 1730 is attached to base 1710 by a hinge 1735, which allows the stylus to be easily retracted and diamond 1701 to be exchanged for a different gemstone. A hood 1720 covers diamond 1701. Hood 1720 can be transparent or can diffusely transmit incident ambient light. In some embodiments, hood 1720 includes one or more light shaping elements to manipulate transmitted ambient illumination to provide desirable illumination conditions for diamond 1701 (e.g., see example discussed below).

Reflecting surface 1740 is hemispherical in shape and includes three concentric portions 1741-1743 of different color. An aperture 1783 in reflecting surface 1740 allows light reflected toward a pole of the hemisphere to pass through the hemisphere into base 1710.

Base 1710 includes mirrors 1711 and 1712 which direct light passing from diamond 1701 via aperture 1783 through an imaging optic 1713 so that an image of diamond 1701 can be observed through an eyepiece lens 1714. Eyepiece lens 1714 can be adjustable to provide variable focus for a observer.

Rays 1781 of ambient illumination are incident at locations 1721 and 1722 on hood 1720. Hood 1720 scatters incident light so that light incident at locations 1721 and 1722 is incident at multiple different locations of reflecting surface 1740. Some rays are reflected by portion 1741 towards diamond 1701. The rays from portion 1741 incident on the diamond 1741 are of a first color, corresponding to the color of portion 1741. Similarly, rays reflected from portions 1742 and 1743 will have second and third colors, respectively. Diamond 1701 directs some of the incident rays through aperture 1783 to contact mirror 1711. Mirror 1711 reflects the light towards mirror 1712, which directs the light through optic 1713 and eyepiece 1714. The light exits eyepiece 1714, as indicated by ray 1784, where it forms an image of diamond 1701. The image is composed of the colors of portions 1741-1743. The image can also include light leaked by diamond 1701, which can appear as white light in the image, corresponding to the spectrum of ambient illumination.

Figure 7B:
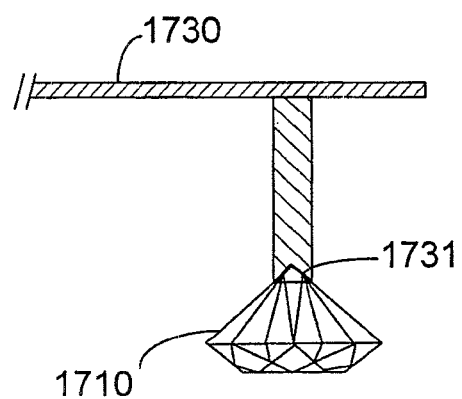
FIG. 7B is a diagram of a stylus used to position a diamond within the illumination apparatus shown in FIG. 7A.

Referring to FIG. 7B, stylus 1730 can include an indentation 1731 at the end for accepting the diamond's culet. Stylus 1730 centers diamond 1701 with respect to the hemisphere of reflecting surface 1740, and can accommodate different diamond shapes.

Figure 7C:
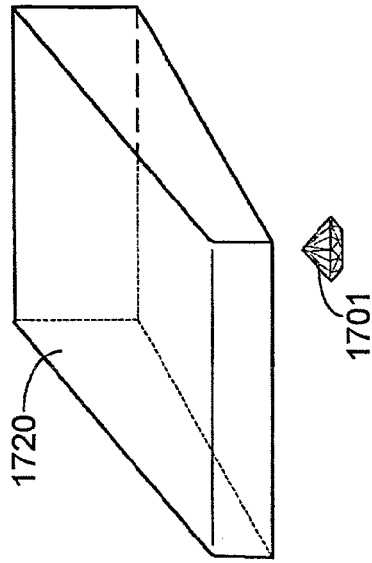
FIG. 7C is a diagram of a cover portion of the illumination apparatus shown in FIG. 7A.

A perspective view of hood 1720 is shown in FIG. 7C. Hood 1720 should, in general, provide uniform illumination to reflecting surface 1740. In some embodiments, hood 1720 can include one or more optical elements to refract, diffract, reflect, absorb, and/or filter ambient illumination. For example, referring to FIGS. 8A-8D, hood 1720 can include a microlens array 1800, which includes multiple refractive elements to focus ambient illumination incident thereon.

Figure 8A:
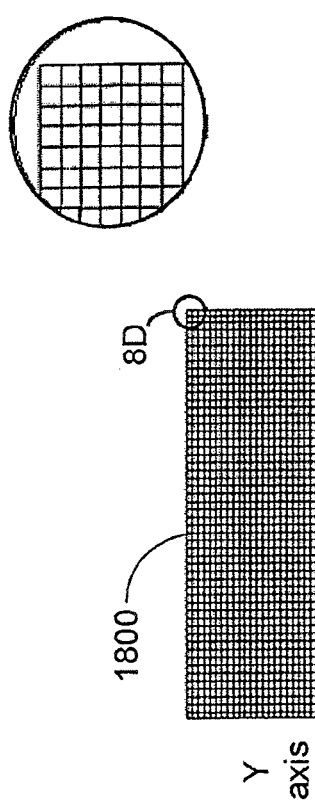
FIGS. 8A-8D are diagrams showing different views of a lenslet array that can be used to form the cover portion shown in FIG. 7C.
Figures 8B, 8C:
Figure 8D:

Examples of refractive elements are shown in cross-section through orthogonal planes in FIGS. 8B and 8C. Microlens array 1800 can homogenize illumination transmitted by hood 1720. In general, optical elements can be used to gather and distribute incident ambient light to provide uniform illumination to reflecting surface 1740.

Figure 9:
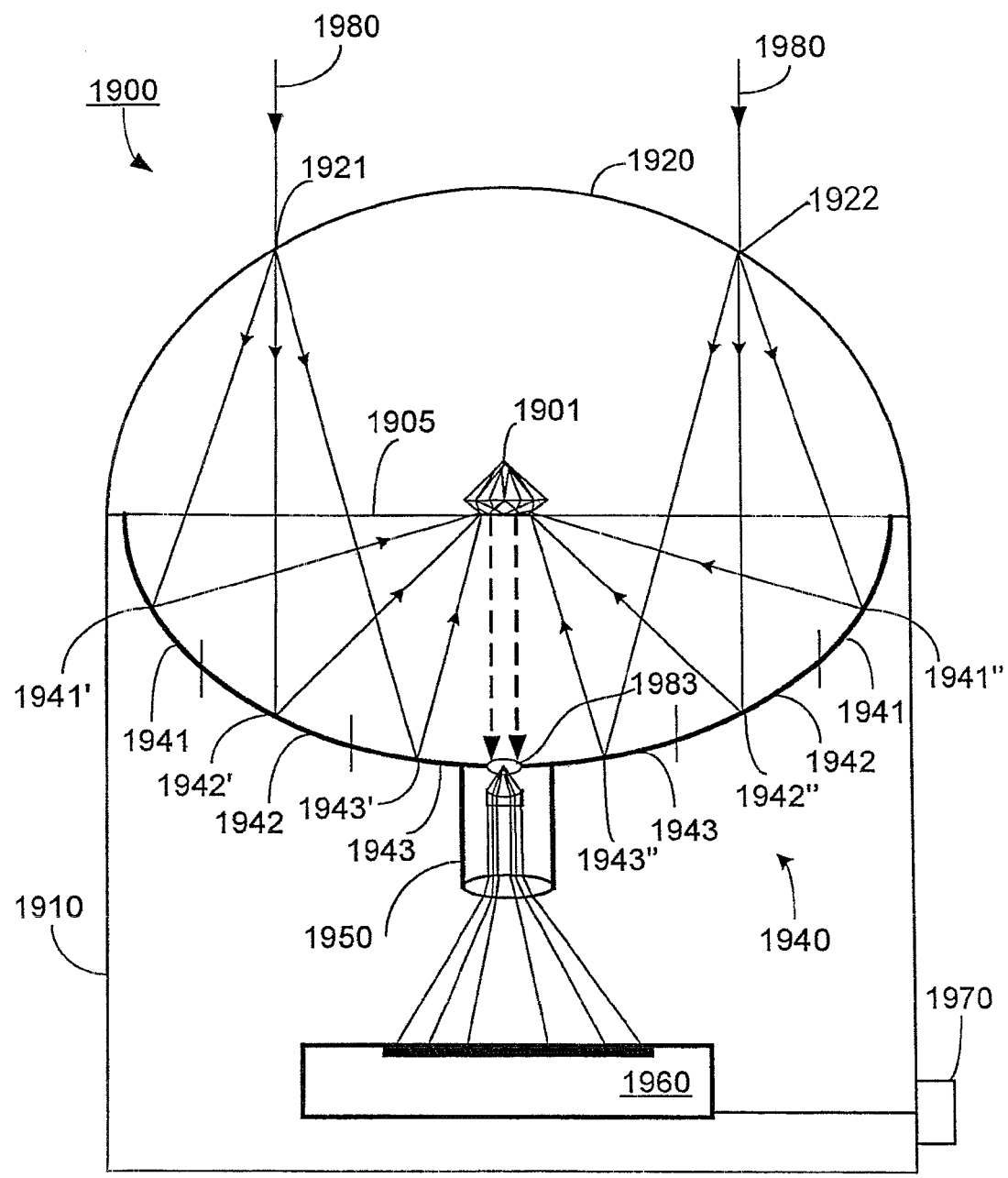
FIG. 9 is a diagram of an embodiment of an illumination apparatus for evaluating a diamond.

Referring to FIG. 9, another embodiment of an illumination apparatus 1900 that utilizes ambient illumination includes a base 1910 and a reflecting surface 1940 that directs light transmitted by a hood 1920 towards a diamond 1901 positioned on a gemstone stage 1905. Imaging optics 1950 located relative to an aperture 1983 in reflecting surface 1940 image diamond 1901 onto an image capture device 1960 (e.g., a CCD or CMOS camera). Image capture device 1960 can communicate to an external processor (e.g., a computer) via a port 1970.

In certain embodiments, reflecting surface 1940 includes three concentric portions 1941, 1942, and 1943, which each reflect light of a different color towards diamond 1901, Rays 1980 of ambient illumination are incident at locations 1921 and 1922 on hood 1920. Incident light is scattered into multiple directions and rays are directed to multiple locations of reflecting surface 1940. Some rays, e.g., those incident at location 1941' and 1941", are reflected by portion 1941 towards diamond 1901. The rays from portion 1941 incident on the diamond 1901 are of a first color, corresponding to the color of portion 1941. Similarly, rays reflected from portions 1942 (e.g., at locations 1942' and 1942") and 1943 (e.g., at locations 1943' and 1943") will have second and third colors, respectively. Diamond 1901 directs some incident rays through aperture 1983, which are imaged by imaging optics 1950 onto detector 1960. The image can be magnified.

While color-coded images of diamonds like the image shown in FIG. 5A, can be acquired optically as described above, such images can also be generated computationally using, for example, commercially available optical design programs such as ASAP™ (available from Breault Research Organization, Tucson, Ariz.), FRED (available from Photon Engineering, Tucson, Ariz.), LightTools® (available from Optical Research Associates, Pasadena, Calif.), TRACEPRO® (available from Lambda Research, Littleton, Mass.) or ZEMAX® (available from ZEMAX Development Corporation, San Diego, Calif.).

Figure 10:
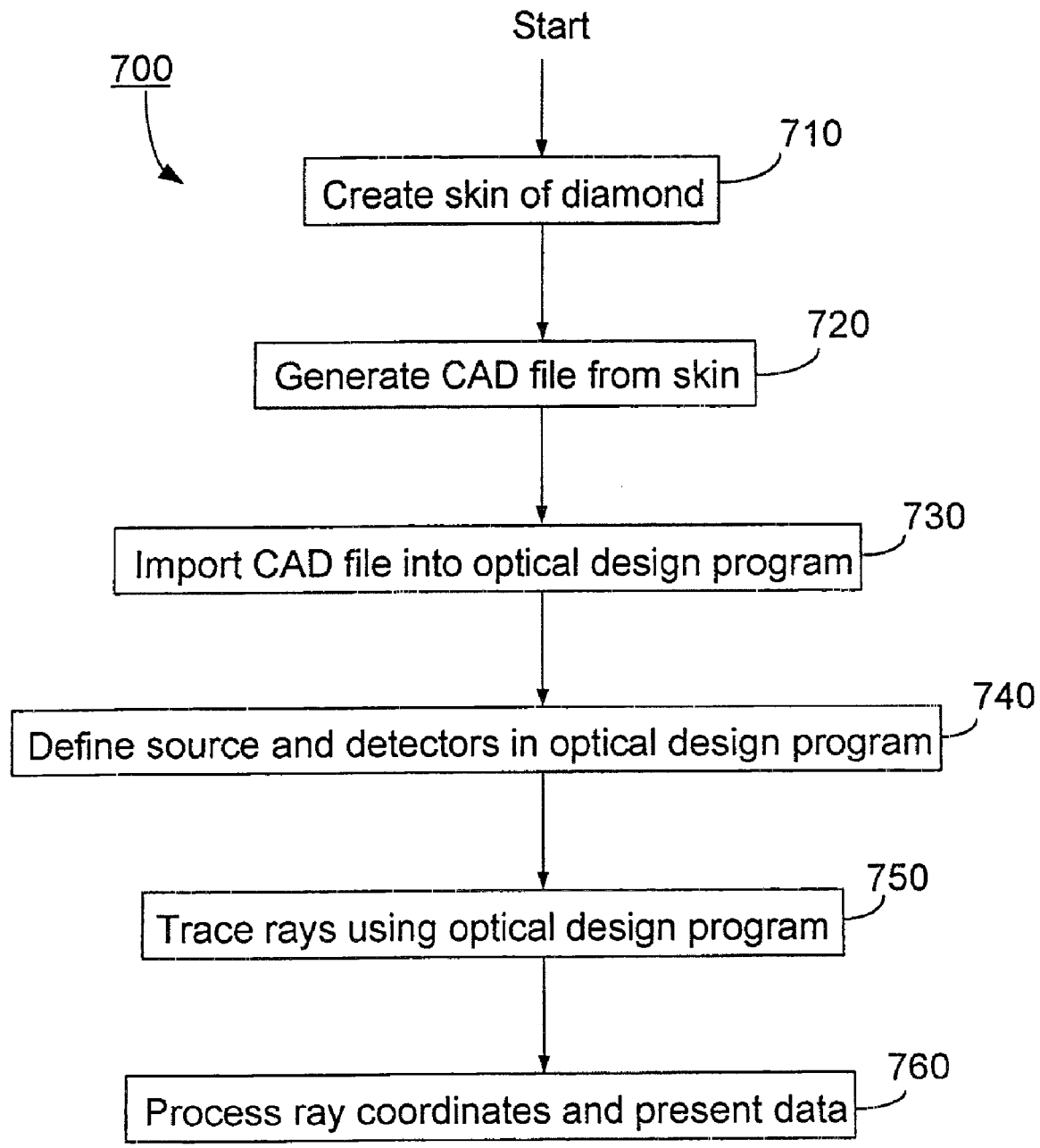
FIG. 10 is a flow chart summarizing steps in a process for producing a color-coded image of a diamond using an optical design computer program.

Referring to FIG. 10, a method for computationally generating a color-coded image of a diamond is summarized in flow chart 700. The first step is to create a "skin" of the diamond (step 710). A "skin" refers to a data set including information about the diamond's geometry, such as the size and shape of each facet, and facet angles and locations. A skin may be acquired using a DiaMension™ tool running DiaVision™ software, both available from Sarin Technologies Ltd. (Sarin USA, New York, N.Y.). The DiaMension™ tool includes a camera, a lens body, a stage for positioning the diamond relative to the camera. The tool has accompanying software that allows a user to interface with the tool using a computer. Using DiaVision™ software, the computer generates the skin from images of the diamond, and outputs the skin in a "SRN" file format.

Once the skin is acquired, it is converted into a file format that can be used in an optical design program (Step 720). This can be performed using DiamCalc diamond calculator available from OctoNus Software Ltd. (Moscow, Russia), which converts the SRN file into a STL format file (stereolithograph file), which can be accessed by ZEMAX®, for example. Examples of other file formats used by optical design programs include computer-aided design (CAD) formats, such as DXF and IGES formats. The converted file is then imported into the optical design program (step 730).

Prior to tracing ray paths through the diamond, the user defines a source and detectors in the optical design program (step 740). The source can be a point source or a spatially extended source. The source can be monochromatic, colored (e.g., include multiple wavelengths in a wavelength band that is a subset of the visible spectrum), or a broadband source (e.g., including multiple wavelengths across the entire visible spectrum). In general, more wavelengths included in the source will increase the computational cost of the process. In some embodiments, a monochromatic source is selected for computational efficiency. In other embodiments, more than one wavelength is selected. For example, where dispersive effects are to be considered, two or more wavelengths can be used.

In general, the location of the source with respect to the diamond can vary. In some embodiments, rays can be traced for a diamond facing the source (e.g., where the source is located along a normal to table as measured from the center of the table). Alternatively, or additionally, rays can be traced with the diamond tilted with respect to the source. For example, the diamond can be tilted about 2° or more with respect to the source (e.g., about 3° or more, about 4° or more, about 5° or more, about 6° or more, about 7° or more, about 8° or more, about 9° or more, about 10° or more, about 11° or more, about 12° or more, about 13° or more, about 14° or more, about 15° or more, about 17° or more, about 20° or more).

The distance between the source and the diamond can also vary. Typically, the source is located between about one centimeter and about 100 centimeters from the diamond (e.g., between about 20 centimeters and 40 centimeters, such as about 25 centimeters).

Figure 11:
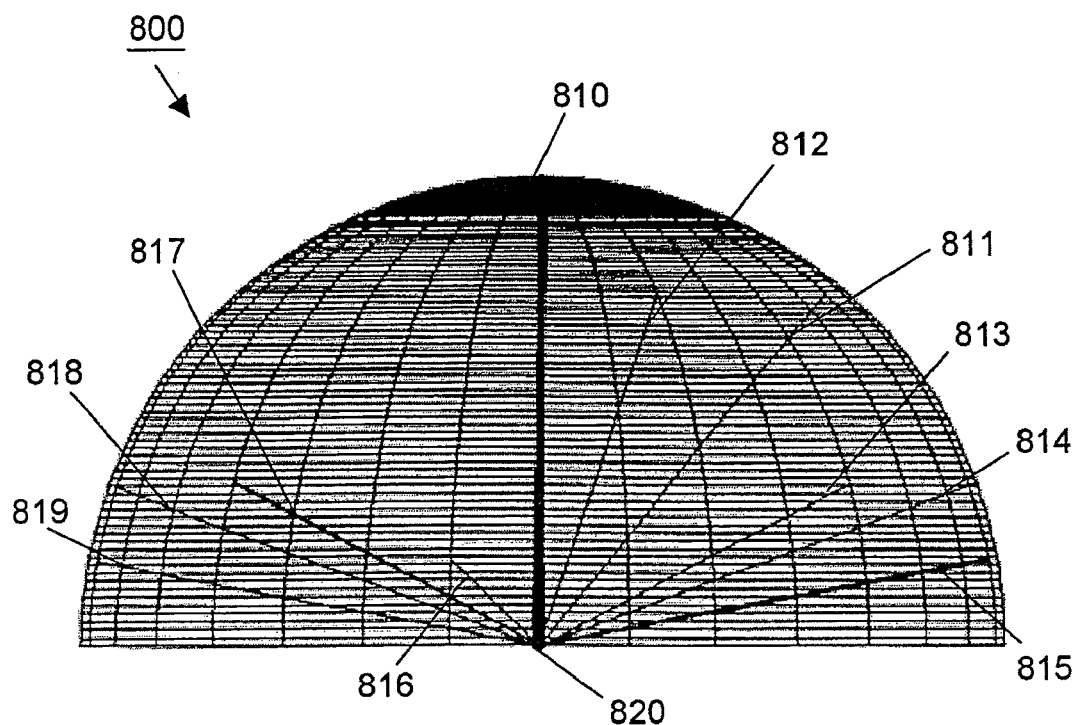
FIG. 11 is a schematic diagram of a hemispherical detection grid used to produce a color-coded image of a diamond using an optical design computer program.

Defining the detectors in the optical design program refers to defining a surface within a reference frame where rays traced through the diamond are collected. In other words, the ray-tracing algorithm will record the location where a ray intersects a surface defined by the detector locations. In general, the geometry of the surface may vary as desired. As an example, in some embodiments, rays are collected on a surface of a hemisphere centered on the diamond. An example of such a hemisphere is depicted in FIG. 11. Hemisphere 800 collects light rays in concentric rings at one degree angular spacing for a total of 90 rings. The source is located at a pole 810 of hemisphere 800, while the diamond is located at its center 820. As discussed previously, the orientation of the diamond with respect to the source may vary as desired.

In general, the radius of hemisphere 800 may vary as desired. For example, the radius of hemisphere 800 can be between about one centimeter and about 100 centimeters from the diamond (e.g., between about 20 centimeters and 40 centimeters, such as about 25 centimeters). In this example, the distance between the source and diamond is the same as the radius of hemisphere. However, in other embodiments, the distance between the source and diamond may be different from the radius of hemisphere. Optionally, an additional surface (e.g., a planar surface) can be defined to collect rays that exit the diamond along a path that does not intersect hemisphere 800.

In certain embodiments, detection locations can correspond to surfaces other than a hemisphere. For example, detection locations can correspond to one or more planar surfaces, such as surfaces that define a cubic or rectangular box. In some embodiments, detection locations can correspond to a spherical surface. The diamond can be positioned at the center of the spherical surface, or at other location within the sphere.

Once the source and detectors have been defined, a computer algorithm traces rays through the diamond (step 750, see FIG. 10). The rays originate from the source, interact with the diamond, exit the diamond, and are collected when they reach a collection location. The algorithm can launch rays in different directions at random or systematically. Typically, rays are launched within a cone of directions corresponding to the area of the diamond exposed to the source. This can ensure that all rays that are traced contact the diamond, increasing computational efficiency.

The algorithm traces rays based on physical laws that describe the interaction of electromagnetic radiation with matter. For example, the algorithm can trace each ray based on Snell's law of refraction and/or the law of reflection, which predict the path of a ray at an interface between two media.

The algorithm can account for ray splitting, for example, due to Fresnel reflections at an interface between two media. In some embodiments, the algorithm can account for multiple ray splittings, for example, due to higher order reflections. In other words, where a ray is partially reflected at an interface between two media, the algorithm can trace rays corresponding to both the transmitted portion and the reflected portion of the incident ray. Where the reflected portion is incident on another interface, it can again be split into a transmitted and reflected portion. The algorithm can continue to trace the second order reflection (i.e., the ray corresponding to the reflected portion of the initially reflected ray). A user can specify to what order reflections should be traced. In some embodiments, second order or higher reflections can be traced (e.g., third order or higher, fourth order or higher, fifth order or higher).

The algorithm can record the locations at which each ray intersects facets of the diamond For example, the algorithm records where each ray intersects the diamond's crown (e.g., table and/or bezel).

Referring again to FIG. 11, illustrative ray paths 811-819 are shown. In general, a sufficient number of rays to provide meaningful data should be traced. In some embodiments, the number of rays traced can be relatively large (e.g., about 100,000 or more, about 500,000 or more, about 1,000,000 or more). For example, in embodiments where one or more images of the diamond are to be generated, a sufficiently large number of rays to fill the image should be used. However, in certain embodiments, fewer rays can be traced (e.g., about 50,000 or less, about 20,000 or less, such as about 5,000). For example, when calculating one or more attributes of the diamond (e.g., fire, or a percentage of rays arriving from a certain range of angles), about 5,000 to about 50,000 rays can provide sufficiently accurate results.

In order to generate an image of the gemstone, the rays detected at the hemisphere can be reverse traced. In other words, the collection locations are treated as source points, and the source is treated as the collection location. The image of the diamond is then generated by identifying rays originating from the different angular ranges and identifying which portions of the diamond they pass through en route to the original source point. Portions corresponding to rays originating from the first range of directions are colored red in the image, portions corresponding to rays originating from the second range are colored blue, and portions corresponding to rays originating from the third range are colored green. The computer-generated image can then be analyzed as discussed above for the real image.

Figures 12A, 12B, 12C:
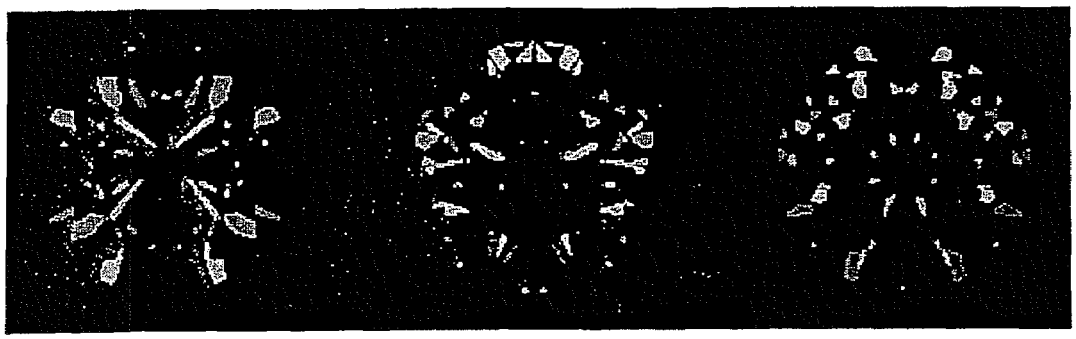
FIGS. 12A-12C are color-coded images of a diamond generated from a skin.

Referring to FIGS. 12A-12C and FIG. S. 13A-13C, computer-generated images can be produced for configurations in which the diamond's table normal is not aligned with pole 810, which correspond to images of diamond 101 tilted with respect to axis 250 using illumination apparatus 110. Referring specifically to FIGS. 12A-12C, these images were generated for a diamond skin using ZEMAX®, where the illumination corresponded to a 1 mm band of white light located 25 cm from the diamond at an angle of 30° with respect to an observer. In FIG. 12A the diamond's table normal is oriented 5 away from pole 810, while in FIGS. 12B and 12C, the table normal is oriented 10° and 15° away from pole 810, respectively.

Figures 13A, 13B, 13C:
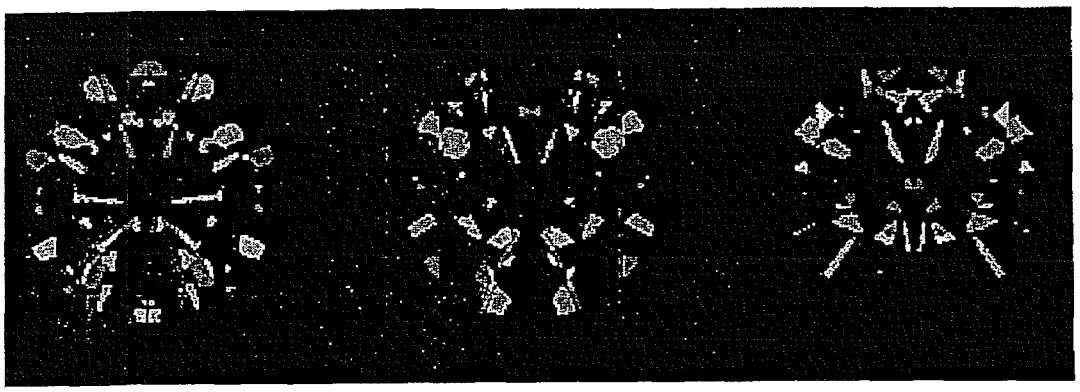
FIGS. 13A-13C are additional color-coded images of a diamond generated from a skin.
Figures 14A, 14B, 14C, 14D:
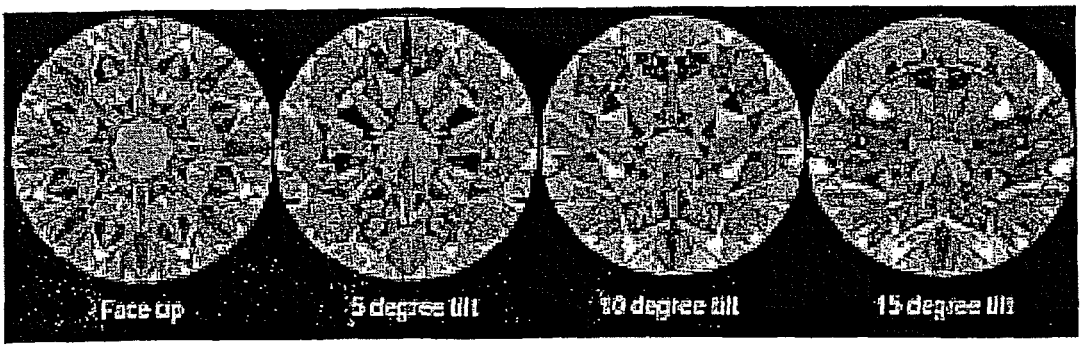
FIGS. 14A-14D are further color-coded images of a diamond generated from a skin

FIGS. 13A-13C were also generated using ZEMAX® and correspond to the same diamond skin used to generate FIGS. 12A-12C at orientations of 5°, 10°, and 15°, respectively, under different illumination conditions.

Referring to FIGS. 14A-14D, in another example, images of a diamond at four different orientations were generated using DiamCalc. The images in FIGS. 14A-14D were generated from the same skin as those images shown in FIGS. 12A-C and FIGS. 13A-C. Here, where green corresponds to a polar angle range of 0°-45°, red corresponds to 45°-75°, and blue corresponds to 75°-90°. FIGS. 14A, 14B, 14C, and 14D correspond to orientations of the diamond's table normal aligned with pole 810, at a 5° tilt, a 10° tilt, and a 15° tilt with respect to pole 810, respectively. The images illustrate how the diamond's appearance changes as it is tilted with respect to an observer.

Figure 15:
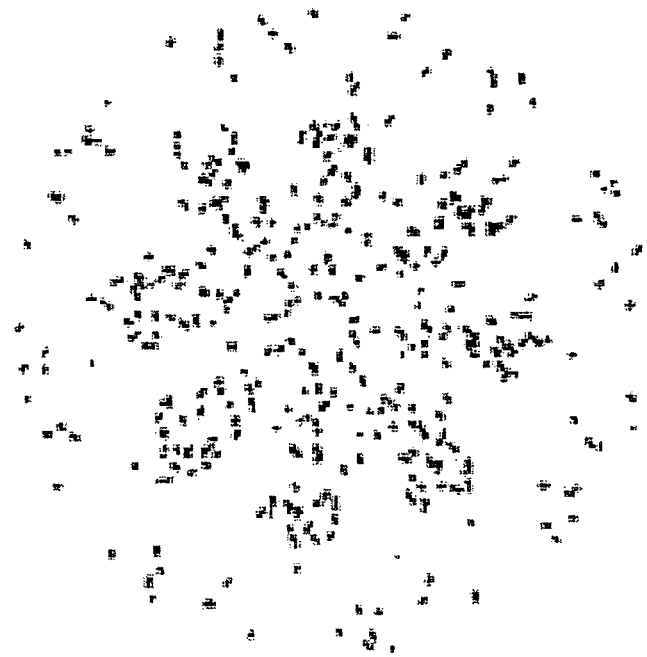
FIG. 15 is an example of an angular spectrum of a diamond produced using an optical design computer program.

The color-coded images described above are one type of representation of which incident ray direction a diamond directs to an observer. Alternatively, or additionally, the data generated using an optical design program can be represented in one or more other formats. For example, another representation of how a diamond gathers light it directs to an observer is an angular spectrum. An angular spectrum refers to a graphical representation showing the set of incident ray directions that the diamond directs to an observer. Referring to FIG. 15, in some embodiments, the angular spectrum of a diamond can be represented by a two dimensional map when these directions are projected onto a hemisphere centered on the diamond. The center of the map corresponds to rays incident on the diamond with a polar angle of 90°. The outer edge of the map corresponds to a polar angle of 0°.

Figure 16A:
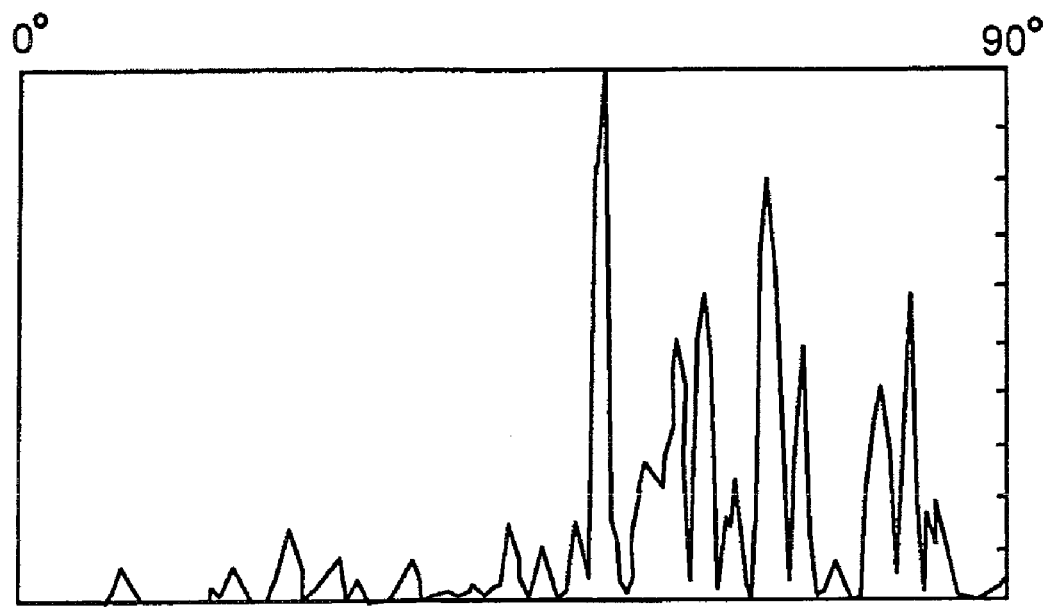
FIG. 16A and FIG. 16B are examples of integrated angular spectra.

Referring to FIG. 16A, an angular spectrum can be integrated over the azimuth, 0, to provide an integrated angular spectrum. An integrated angular spectrum can be represented as an x-y chart with intensity (y-axis in FIG. 16A) plotted as a function of polar ray angle (x-axis in FIG. 16A). The relative intensity refers to the proportion of rays at each polar ray direction. An integrated angular spectrum provides comparable data to the color-coded image. For example, with reference again to FIGS. 2A and 2B, the total number of rays falling within polar angle range 221 corresponds to the amount of red in the color-coded image. Similarly, the total number of rays falling within polar angle range 222 correspond the proportion of blue in the color-coded image of the diamond, and the total number of rays falling within polar angle range 223 correspond the proportion of green in the color-coded image. Accordingly, the diamond can be graded according to the angular spectrum as described previously for the color-coded image.

While data generated using an optical design program can be used to evaluate a diamond's brilliance, contrast, leakage, and scintillation as described previously, it can also be used to evaluate other aspects of a diamond's appearance. For example, ray tracing at different wavelengths can be used to evaluate a diamond's dispersive effects on illumination it directs to an observer. As mentioned previously, where the effects of dispersion are such that a facet directs only a portion of the visible spectrum to an observer's eye, that facet will appear colored under those conditions and will contribute to the diamond's fire.

In some embodiments, a diamond's fire can be evaluated by comparing angular spectra generated at two different wavelengths. One of the two different wavelengths can correspond to a wavelength in the blue portion of visible spectrum (e.g., between about 400 nm and 500 nm, such as about 450 nm). The other wavelength can correspond to a wavelength in the red portion of the visible spectrum (e.g., between about 600 nm and 700 nm, such as about 650 nm). Large differences between the angular spectra at the two wavelengths can indicate substantial dispersion in the diamond and can correspond to a large amount of fire.

Figure 16B:
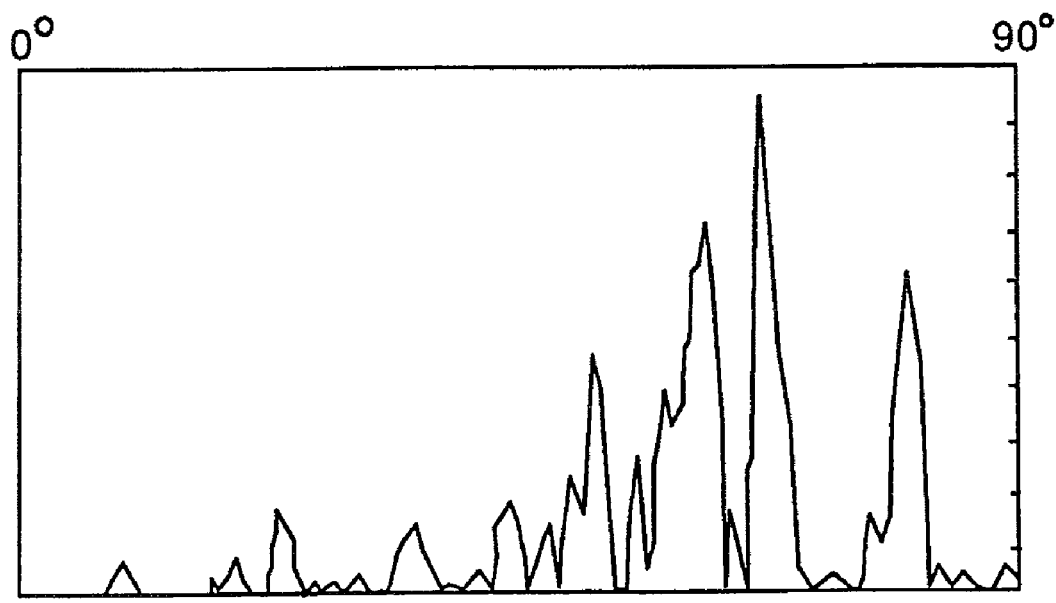

FIG. 16B shows an example of the difference between an integrated angular spectrum determined for a diamond at 487 nm and an integrated angular spectrum determined for the same diamond at 657 nm. In this example, there is a relatively large difference between the integrated angular spectra from about 45° and about 75°.

In some embodiments, fire can be evaluated by tracing one or more pairs of rays, rays in each pairs being incident on the diamond from the same direction but having different wavelengths, and determining the angular difference in the direction of the ray in each ray pair exiting the diamond. The angular difference can be determined from the location on hemisphere 800 that each ray strikes.

In general, the difference between the wavelengths of the rays in each ray pair can vary as desired. In some embodiments, the difference between the wavelengths of the rays in each ray pair can be relatively small (e.g., about 1-10 nm). For example, in some embodiments, the wavelengths of rays in a ray pair can be 519 nm and 521 nm, respectively. Alternatively, the difference between the wavelengths of the rays in each ray pair can be relatively large (e.g., about 50 nm or more, about 100 nm or more). An example of a relatively large difference, the wavelengths of the rays in a ray pair can be 487 nm and 657 nm, respectively.

A value for angular ray dispersion, $D_\theta$, can be calculated for each ray pair from $$D_\theta = K_\theta(\hat{\theta}_1 - \hat{\theta}_2)$$

where $\hat{\theta}$ and $\hat{\theta}$ refer to the angular direction vectors for the first and second ray in a ray pair, respectively, and $K_\theta$ is a normalizing constant. Alternatively, or additionally, dispersion can also be expressed as a positional ray dispersion, $D_x$, given by $$D_x = K_x(\hat{x}_1 - \hat{x}_2)$$

where $\hat{x}_1$ and $\hat{x}_2$ refer to the co-ordinates at which the first and second rays strike hemisphere 600, respectively. $D_\theta$ and/or $D_x$ can be averaged over multiple (e.g., thousands) of ray pairs to provide a measure of average dispersion of the diamond.

Dispersion (e.g., average angular ray dispersion and/or average positional ray dispersion) can be calculated for different portions of a diamond. For example, dispersion can be calculated individually for the table, the inner bezel, and/or the outer bezel. Accordingly, the diamond's fire can be evaluated for different portions of the diamond.

Where average $D_x$ and/or average $D_\theta$ are relatively large (e.g., about the same or more than a Tolkowsky diamond), the diamond can be assigned a good grade for fire. In some embodiments, an average $D_x$ of about 3.0 mm or more (e.g., about 3.2 mm or more, about 3.5 mm or more, about 3.8 mm or more, about 4.0 mm or more) measured on a hemisphere of radius 25 cm, and/or an average $D_\theta$ of about 0.75° or more (e.g., about 1.0° or more, about 1.2° or more) can receive a good grade for fire. Alternatively, where average $D_x$ and/or average $D_\theta$ are relatively small (e.g., average $D_x$ of about 2.5 mm or less, about 2.0 mm or less, about 1.5 mm or less, average $D_\theta$ of about 0.5° or less, about 0.3° or less, about 0.2° or less, about 0.1° or less), the diamond can be assigned a poor grade for fire.

Figure 17:
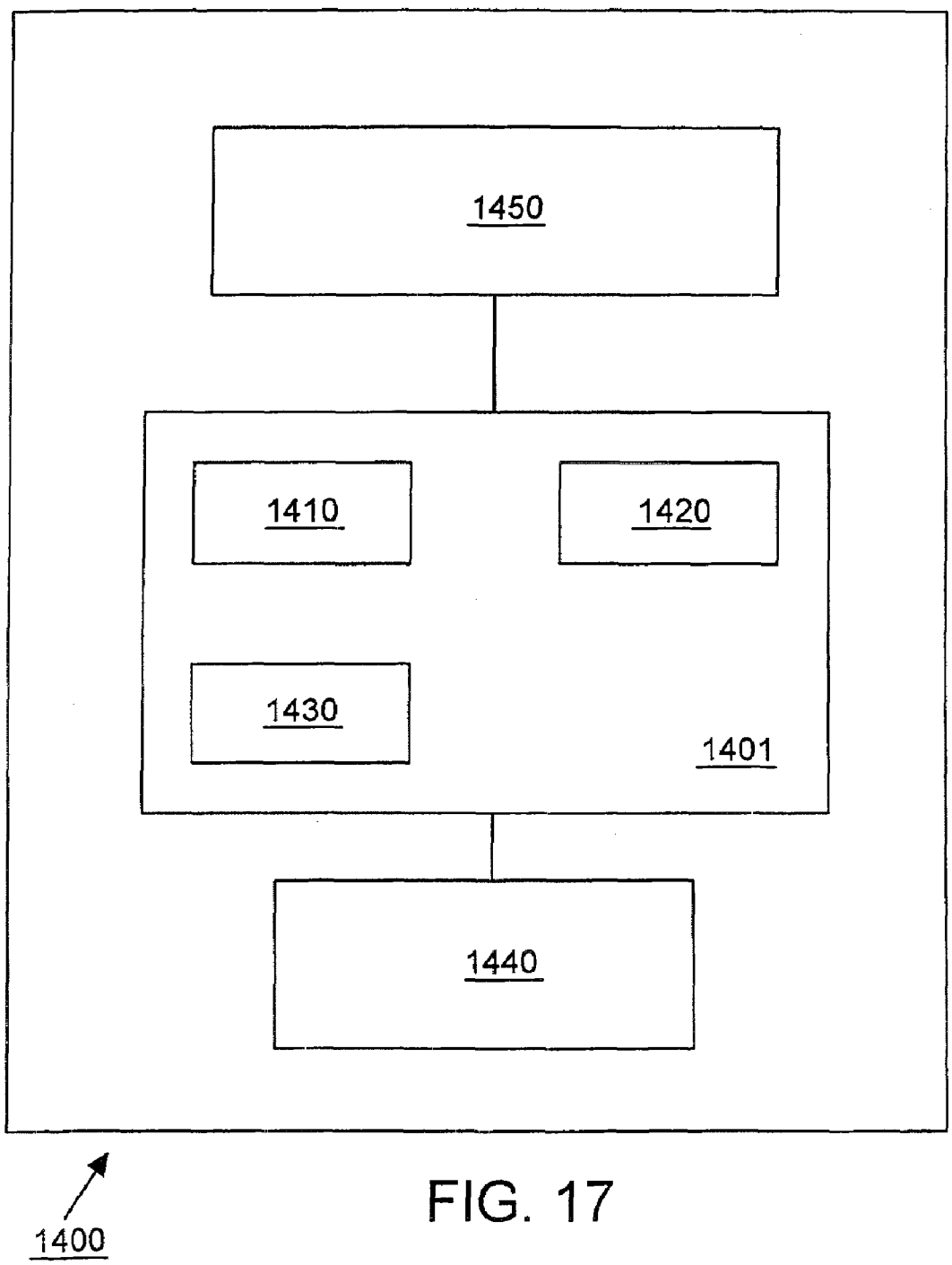
FIG. 17 is a block diagram of a computer.

FIG. 17 shows a computer 1400 for evaluating a diamond using process 500 and/or process 700. Computer 1400 includes a housing 1401, which encloses a processor 1410, a memory 1420 (e.g., random access memory and/or read only memory), a storage medium 1430 (e.g., hard disk). Computer 1400 also includes an input device 1440 (e.g., a keyboard) and an output device 1450 (e.g., an electronic display or printer). To perform process 500, storage medium 1430 stores an operating system, data corresponding to the diamond image, and computer instructions that are executed by processor 1410 out of memory 1430 to perform 500. Similarly, to perform process 700, storage medium 1430 stores an operating system, data corresponding to the diamond skin, and the sources and detectors used by the optical design program, and computer instructions that are executed by processor 1410 out of memory 1430 to perform process 700.

Process 500 and/or process 700 are not limited to use with the hardware and software of FIG. 17; it may find applicability in any computing or processing environment and with any type of machine that is capable of running a computer program. Process 500 and/or process 700 may be implemented in hardware, software, or a combination of the two. Process 500 and/or process 700 may be implemented in computer programs executed on programmable computers/machines that each include a processor, a storage medium/article readable by the processor (including volatile and non-volatile memory and/or storage elements), at least one input device, and one or more output devices. Program code maybe applied to data entered using an input device to perform process 500 and/or process 700 and to generate output information.

Each such program may be implemented in a high level procedural or objected-oriented programming language to communicate with a computer system. However, the programs can be implemented in assembly or machine language. The language-may be a compiled or an interpreted language. Each computer program may be stored on a storage medium (article) or device (e.g., CD-ROM, hard disk, or magnetic diskette) that is readable by a general or special purpose programmable computer for configuring and operating the computer when the storage medium or device is read by the computer to perform process 500 and/or process 700. Process 500 and/or process 700 may also be implemented as a machine-readable storage medium, configured with a computer program, where upon execution, instructions in the computer program cause the computer to operate in accordance with process 500 and/or process 700.

In some embodiments, the methods used for diamond evaluation described herein can be adapted to assist a diamond polisher in cutting and polishing a diamond. For example, given the size, shape, and proportions of an uncut diamond, a user can generate skins corresponding to diamonds that could be cut from the uncut diamond. By evaluating the skins, one can determine which possible cuts will yield diamonds with desirable characteristics (e.g., which cuts will yield a stone with the highest grade for brilliance, scintillation, and/or fire). Based on this assessment, the polisher can increase (e.g., maximize) the value of the uncut diamond by cutting diamonds with appealing characteristics.

A polisher can also utilize an evaluation system, such as system 100, while cutting and/or polishing a diamond. For example, a polisher can compare the appearance of the diamond as viewed using the evaluation system to the image generated using a skin to assess whether appropriate cuts have been made. A polisher can use computer generated color-coded images to show a customer the potential appearance and/or grade of a diamond prior to cutting the diamond.

In some embodiments, the methods discussed herein are used to generate a database of diamond grades for one or more characteristics for different parameters of a diamond's cut. Alternatively, or additionally, the methods discussed herein can be used to generate a database of representations of a diamond's appearance (e.g., color-coded image, angular spectrum, integrated angular spectrum or some other representation) for different parameters of a diamond's cut. These parameters include the absolute and relative size of different portions of a diamond (e.g., table, bezel, girdle, culet, and pavilion) and characteristic angles of diamond (e.g., pavilion angle, crown angle). Such databases can be used to identify diamond cut proportions that provide desirable attributes. For example, where a person desires a diamond with good brilliance, but is not concerned with good fire, they can identify the proportions corresponding to a high grade for brilliance, but not necessarily for fire, and cut the diamond accordingly.

Figure 18:
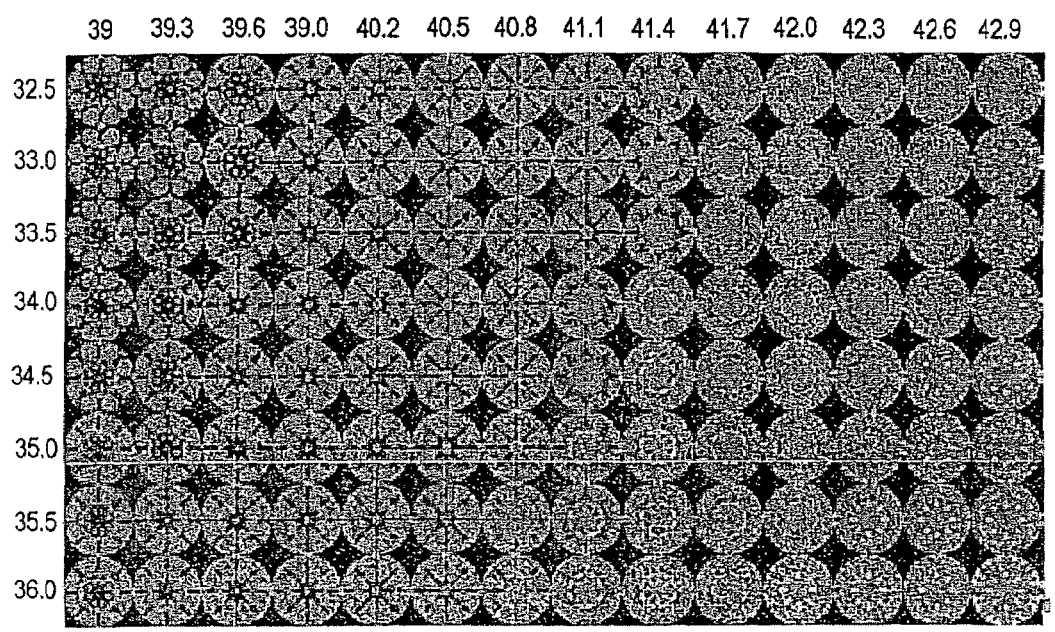
FIG. 18 is a matrix of color-coded images of diamonds having different cuts.
Figure 19A:
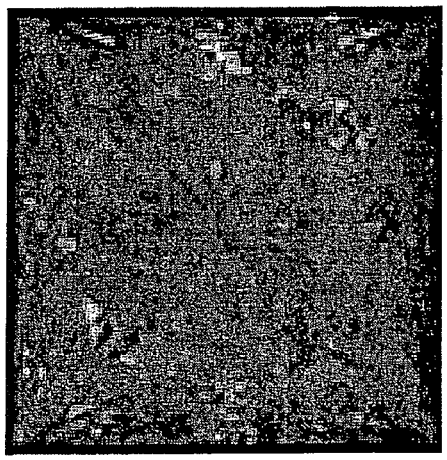
FIGS. 19A-19E are photographs of different princess cut diamonds acquired using an illumination apparatus.
Figure 19B:
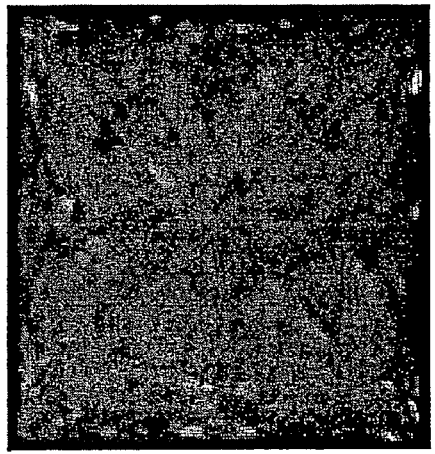
Figure 19C:
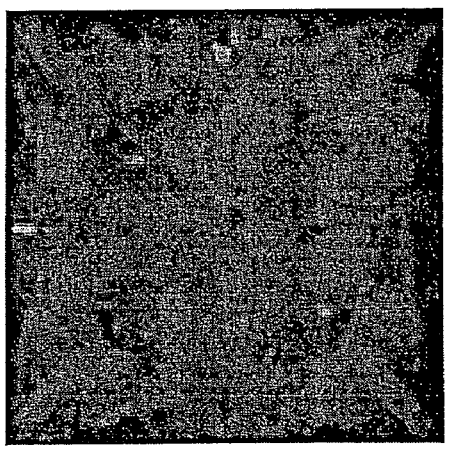
Figure 19D:
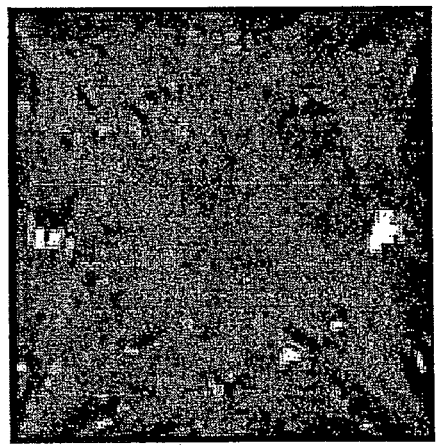
Figure 19E:
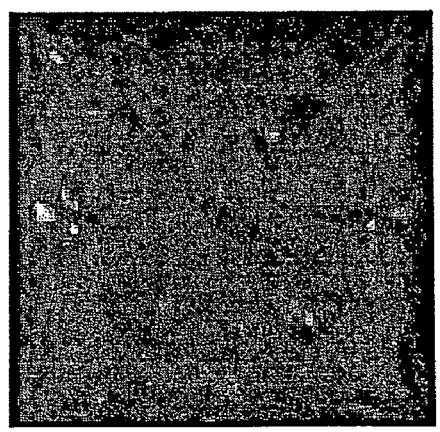
Figure 20A:
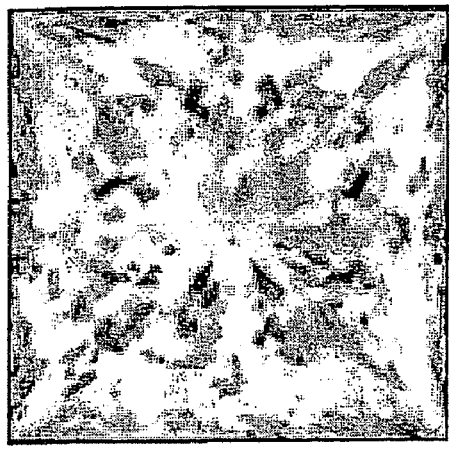
FIGS. 20A-20E are photographs of the different princess cut diamonds shown in FIGS. 19A-19E acquired while illuminating the diamonds with broadband light. Like reference symbols in the various drawings indicate like elements.
Figure 20B:
Figure 20C:
Figure 20D:
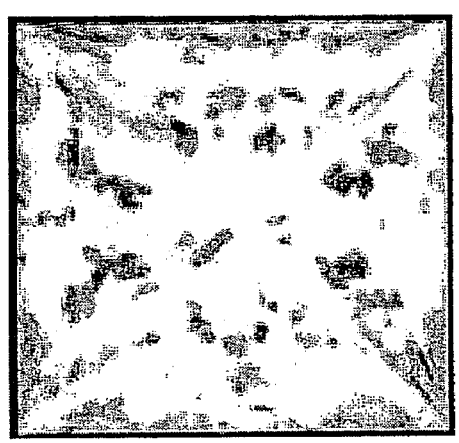
Figure 20E:
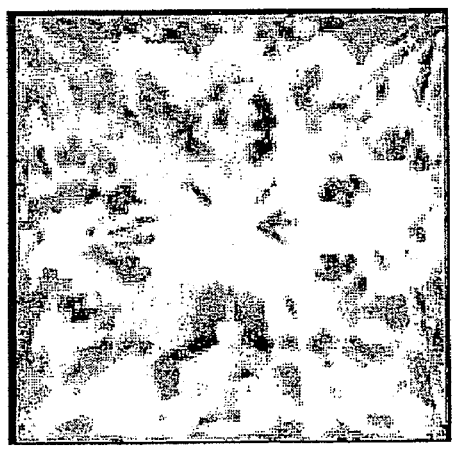

Referring to FIG. 18, an example of such a database is a matrix of color-coded images with rows and columns corresponding to different values for two different cut parameters of a brilliant, round cut diamond. In this example, the columns of the matrix correspond to different values for the pavilion angle and the rows of the matrix correspond to different values of crown angles. Using the matrix, a person can identify the values for pavilion and crown angle corresponding to the desired diamond appearance based on the proportions and distributions of the colors in the color-coded images.

In general, a diamond can be graded based exclusively on its optical performance factors (e.g., brilliance, contrast, fire, scintillation), or based on optical performance factors in combination with other factors. Other factors include, for example, the diamond's weight, cut, color, and clarity. An example of another factor is the diamond's spread, which is related to the cut and weight of the diamond. In particular, spread refers to the ratio of the birds-eye-view area of a diamond to its weight.

Spread can be quantified as a scaled weight, which is the diamonds actual weight multiplied by a factor related to the diamond's cut proportions. The factor scales the weight of the diamond to by an amount related to departures of the diamond's proportions from a diamond of similar weight and cut that has ideal proportions, i.e., an optimal spread. As an example, in some embodiments, the scaled weight, $W_s$, can be given by:

$$W_s = W \times \left(\frac{\sqrt{A_i}}{\sqrt{A}}\right)^3,$$

where W and A are the actual weight and birds-eye-view area of the diamond, respectively, and $A_i$ is the birds-eye-view area of a similar weight diamond with ideal proportions. For example, a princess cut diamond that is 1.45 carats in weight is, in certain estimations, ideally 6 mm by 6 mm in size. Generally, a 1.45 carat princess cut diamond that has a larger area will not appear as attractive, and its grade should be reduced accordingly.

A diamond can be given individual grades for each of a number of factors. A diamond is given a single grade that accounts for more than one factor. A diamond can be given an initial grade (e.g., on a numeric and/or alphabetic scale), and the initial grade can be adjusted based on one or more factors. For example, the initial grade can correspond to an ideal diamond, and the initial grade can be reduced an amount for one or more factors depending on how much each factor deviates from being ideal. The amount of the reduction can increase as the deviation from the ideal increases.

In some embodiments, a deduction for each factor can be determined using a lookup table. This table can include a set of ranges for each factor, and a deduction value corresponding to each range. To determine a deduction for that factor, one looks to see which range the value falls into. The deduction then corresponds to the deduction for that range.

As an example, a diamond's initial grade can be reduced based on the amount of dispersion determined for the diamond, as discussed above. The amount by which an initial grade of 10 is reduced can be calculated based on a lookup table, such as Table 1 below.

TABLE 1

Exemplary deductions for dispersion ranges.

| Dispersion Range [mm] | Deduction |
|---|---|
| 0.0222 or more | 0 |
| 0.0167-0.0221 | 1 |
| 0.0111-0.0166 | 2 |
| 0.0056-0.0110 | 3 |
| 0.0000-0.0055 | 4 |

As a further example, the initial diamond grade can be reduced based on a proportion of a color-coded diamond image that is a certain color. For example, Table 2 shows a deduction scale for a proportion of a color-coded image that appears red, where red corresponds to mid-range illumination directions (e.g., polar angles from 45° to 75°). As discussed previously, for these illumination directions, the amount of red in an image is related to the diamond's brilliance, hence the higher the proportion of red in the image, the lower the deduction

TABLE 2

Exemplary deductions for proportions of mid-angle illumination in an image.

| Percentage of Red in Image | Deduction |
|---|---|
| 40% or more | 0 |
| 30%-39.9% | 1 |
| 20%-29.9% | 2 |
| 10%-19.9% | 3 |
| 0%-9.9% | 4 |

In some embodiments, the initial grade can also be reduced based on a deduction for leakage determined from a color-coded image or other representation. Generally, the leakage deduction increases as leakage increases. An example of deductions for specific leakage ranges is shown in Table 3, below.

TABLE 3

Exemplary deductions for percentage of leaked light.

| Percentage of light leaked by Diamond | Deduction |
|---|---|
| 0.0%-35.0% | 0 |
| 35.1%-45.0% | 1 |
| 45.1%-55.0% | 2 |
| 55.1%-65.0% | 3 |
| 65.1%-75.0% | 4 |
| 75.1%-85.0% | 5 |
| 85.1% or more | 6 |

In some embodiments, factors can be determined for more than one orientation of the diamond (e.g., with respect to a viewer). A subsequent deduction for that factor can be based on the orientation for which the deduction value is smallest or, alternatively, greatest. For example, dispersion can be calculated for a diamond facing the viewer, and also for the diamond tilted 15° relative to the viewer. The initial value of the diamond's grade is reduced by the greater of the two deductions.

In certain embodiments, factors can be determined for more than two orientations. For example, where a stone shape is asymmetric about rotations about an axis normal to the table (e.g., rectangular princess cut diamonds, oval cut diamonds, or marquise cut diamonds), a deduction can be calculated for the diamond tilted along both principle directions (e.g., in the direction of the long and short axes of the diamond) in addition to the untitled orientation. In such cases, the actual deduction can correspond to the greatest of the three deductions.

As discussed previously, another optical performance factor for a diamond is contrast. Accordingly, the diamond's initial grade can also be adjusted based on a value related to contrast. A value for contrast can be determined from the proportion of a diamond's color-coded image that corresponds to high illumination angles (e.g., polar angles of 75° or more). Table 4 shows exemplary deductions corresponding to image percentage ranges corresponding to high illumination angles.

TABLE 4

Exemplary deductions for percentages of high-angle illumination in an image.

| Percentage of Image | Deduction |
|---|---|
| 0.0%-8.0% | 1 |
| 8.1%-22.0% | 0 |
| 22.1% or more | 1 |

In some embodiments, a contrast deduction can be determined for more than one range of illumination directions. The diamond's grade can be adjusted based on the larger of the contrast deductions. For example, a deduction can be calculated from an image where high-angle illumination corresponds to 75° or more according to Table 4, A second deduction can also be determined from an image where the high-angle illumination corresponds to 70° or more, for example, based on Table 5, below. The diamond's grade is adjusted based on the larger of the two contrast deductions.

TABLE 5

Other exemplary deductions for percentage of high-angle illumination in an image.

| Percentage of Image | Deduction |
|---|---|
| 0.0%-30.0% | 0 |
| 30.1%-35.0% | 1 |
| 35.1%-40.0% | 2 |
| 40.1%-45.0% | 3 |
| 45.1%-50.0% | 4 |
| 50.1%-55.0% | 5 |
| 55.1%-60.0% | 6 |
| 60.1%-65.0% | 7 |
| 65.1% or more | 8 |

The diamond's initial grade can also be reduced based on non-optical performance factors, such as the diamond's spread. As discussed previously, spread can be quantified using a scaled weight. Accordingly, a spread deduction can be calculated based on the diamond's scaled weight. Table 6 shows exemplary deductions for the weight of a princess cut diamond scaled according to an ideal princess cut diamond weighing 1.45 carats.

TABLE 6

Exemplary deductions based on scaled weight of 1.45 carat princess cut diamond.

| $W_s$ range [carats] | Deduction |
|---|---|
| 1.450 or less | 0 |
| 1.451-1.566 | 1 |
| 1.567-1.682 | 2 |
| 1.683-1.798 | 3 |
| 1.799-1.914 | 4 |
| 1.915-2.030 | 5 |
| 2.031-2.146 | 6 |
| 2.147-2.262 | 7 |
| 2.263-2.378 | 8 |
| 2.379-2.494 | 9 |
| 2.495 or more | 10 |

An ideal range for a factor (e.g., corresponding to a deduction of zero) can be different for different diamond cuts. Accordingly, deduction tables can be adjusted for different cuts, or entirely different tables can be used depending on a diamond's cut.

Similarly, deduction tables can be adjusted for diamonds having the same cut but different weight. For example, while Table 6 gives exemplary deductions for a 1.45 carat princess cut diamond, the optimal scaled weight for princess cut diamonds of other weights can be different. Accordingly, different deduction tables can be used for diamonds of different weight.

Once values for each factor are determined, the diamonds' grade can be calculated manually (e.g., a grader looks up deductions for each factor on appropriate charts, and calculates the grade from once all the deductions are known) or automatically (e.g., using a computer algorithm).

In general, deduction value tables can be determined empirically. In some embodiments, one can assign deductions to various factors of diamonds that have been evaluated using one or more subjective methods (e.g., by eye). For example, a person skilled in diamond evaluation can look at a number (e.g., several hundred, or thousands) of diamonds, and grade each diamond based on their brilliance. Subsequently, they can determine the proportion of mid-level illumination each diamond directs to an observer, and correlate the grade with the proportion.

In some embodiments, contrast and/or contrast distribution can be evaluated using color-coded image matrices, for example. Regions of the matrices considered to have good contrast and/or contrast distribution can be assigned low deductions (e.g., 0 or 1), while regions considered by graders to have poorer contrast and/or contrast deduction can be assigned larger deductions (e.g., 2 or more, 3 or more, 4 or more). A grader can assign a deduction for contrast and/or contrast distribution by comparing a color-coded image of the diamond to a matrix corresponding to the diamond's cut proportions.

Databases of diamond grades used to correlate diamond grade deductions to their corresponding optical performance factors can include additional information characterizing the diamond, such as symmetry, girdle thickness, polish, and/or culet condition, for example, allowing deduction values to be based on one or more of these additional characteristics.

The methods, apparatus, and systems described herein may be used to evaluate diamonds of different shape, including brilliant, round cut diamonds and fancy cut diamonds. Fancy cut diamonds include marquise, oval, trilliant, radiant, pear-shaped, heart-shaped, princess cut, cushion cut, and emerald cut diamonds. Furthermore, the methods, apparatus, and systems described herein may be adapted to evaluate gemstones other than diamonds (e.g., topaz, emeralds, rubies, quartz), particularly gemstones whose appearance and value are related to their cut and proportions

EXAMPLE

Five princess cut diamonds, referred to as diamonds I-V, were evaluated by acquiring a skin of each diamond using a DiaMension™ tool running DiaVision™ software, both obtained from Sarin Technologies Ltd. (Sarin USA, New York, N.Y.). An "SRN" file was created for each diamond using the DiaVision™ software. For each diamond, a "STL" file was generated from the corresponding "SRN" file using DiamCalc software (obtained from OctoNus Software Ltd., Moscow, Russia). The STL files were ray traced using ZEMAX® obtained from ZEMAX Development Corporation, San Diego, Calif.

A scaled weight was determined for each diamond using the DiaVision™ software using the equation provided above. A spread deduction was then calculated for each diamond using Table 6. Ray tracing was performed for each diamond by first defining a source at a position 25 cm from the diamond, and directing rays to the diamond from the source. Rays emitted from the diamond were collected at a hemispherical shell of radius 25 cm centered on the diamond. The location of the source corresponded to the pole of the hemisphere.

Ray tracing was performed with the diamond in two different orientations with respect to the source. In one orientation, the diamond's table was facing the source, while in the other the diamond was tilted 15° with respect to the source. 24,000 rays were traced with the diamond in each orientation, with 8,000 rays having wavelengths 519 nm, 520 nm, and 521 nm, respectively.

After ray tracing, percentages for the number of rays at 520 nm directed by each diamond into different portions of the hemisphere were calculated for both orientations of the diamond. In particular, the percentage of rays directed at polar angles from 0° to 45° were calculated, where 0° corresponds to the equator of the hemisphere and 90° corresponds to the pole. Also calculated were the percentage of rays directed at polar angles from 45° to 75°, from 70° to 90°, and from 75° to 90°. The percentage of rays directed into each of these ranges is summarized for each diamond in Table 7 and Table 8 below.

The percentage of rays not directed into the hemisphere was also calculated at 520 nm for each diamond, and is summarized in Table 7 and Table 8 under the columns labeled "Leakage."

The rays traced at 519 nm and 521 nm were used to characterize the diamond's dispersion. Dispersion was characterized for three different concentric zones of the diamond, the innermost zone being referred to as the "table," the middle zone being referred to as the "inner bezel," and the outermost zone being referred to as the "outer bezel." For each zone, dispersion was characterized by first identifying rays at 519 nm incident on the diamond within the zone and that were directed by the diamond along paths at polar angles from 45° to 75°. Next, corresponding rays at 521 nm, launched along identical trajectories to the first identified rays at 519 nm were identified. A dispersion value was measured for each ray pair as the separation distance between the locations where the ray pairs intersect the hemisphere. Dispersion values exceeding 2.5 mm were discarded as they likely corresponded to ray pairs that strike different facets within the diamond. The retained values are averaged for each diamond zone in each orientation. These averages are provided in Table 7 and Table 8 below.

TABLE 7

Calculated parameter values for princess cut diamonds I-V oriented with the table facing the source.

| Diamond | Scaled Weight | Table Dispersion [mm] | In. Bezel Dispersion [mm] | Out. Bezel Dispersion [mm] | Rays from 0° to 45° [%] | Rays from 45° to 75° [%] | Rays from 70° to 90° [%] | Rays from 75° to 90° [%] | Leakage [%] |
|---|---|---|---|---|---|---|---|---|---|
| I | 1.36 | 0.022 | 0.024 | 0.042 | 25.3 | 52.6 | 14.3 | 5.3 | 16.8 |
| II | 1.47 | 0.028 | 0.028 | 0.042 | 16.6 | 54.7 | 22.3 | 13.2 | 15.5 |
| III | 1.50 | 0.017 | 0.035 | 0.042 | 9.3 | 57.5 | 29.7 | 17.2 | 16.1 |
| IV | 1.41 | 0.017 | 0.028 | 0.042 | 24.0 | 49.6 | 20.2 | 10.0 | 16.5 |
| V | 1.48 | 0.017 | 0.024 | 0.042 | 18.7 | 53.6 | 23.9 | 11.9 | 15.8 |

TABLE 8

Calculated parameter values for princess cut diamonds I-V measured with table at an angle of 15° to the source.

| Diamond | Table Dispersion [mm] | In. Bezel Dispersion [mm] | Out. Bezel Dispersion [mm] | Rays from 0° to 45° [%] | Rays from 45° to 75° [%] | Rays from 75° to 90° [%] | Leakage [%] |
|---|---|---|---|---|---|---|---|
| I | 0.022 | 0.028 | 0.042 | 21.9 | 39.3 | 10.9 | 16.8 |
| II | 0.028 | 0.028 | 0.047 | 16.3 | 39.1 | 15.3 | 15.5 |
| III | 0.022 | 0.031 | 0.036 | 13.0 | 41.1 | 10.1 | 16.1 |
| IV | 0.022 | 0.028 | 0.036 | 19.6 | 42.2 | 9.4 | 16.5 |
| V | 0.022 | 0.024 | 0.042 | 18.2 | 42.4 | 11.1 | 15.8 |

Grades were assigned to each diamond based on several of the above-mentioned parameters. For the graded parameters, if the parameter value fell into an optimal range, the diamond was assigned a grade of 0 for that parameter. For less than optimal values, the diamond was assigned grades of 1, 2, 3 etc., with the higher numbers corresponding to increasingly undesirable values for the parameters. The grading ranges for different parameters are summarized in Table 9 and Table 10 below. Ultimately, each diamond was assigned a final grade that was calculated by summing the grades for each graded parameter.

TABLE 9

Parameter ranges corresponding to grade deductions. [15°] refers to grades applied to parameters calculated with the diamond oriented at 15° with respect to the source.

| Deduction | Rays from 45° to 75° | Rays from 75° to 90° | Rays from 70° to 90° | Leakage | Rays from 45° to 75° [15°] | Leakage [15°] |
|---|---|---|---|---|---|---|
| 0 | >35% | 8.0%-22.0%* | 22.0%-30.0% | <35.0% | <35.0% | <35.0% |
| 1 | 30.0%-34.9% | — | 30.1%-35.0% | 35.1%-40.0% | 30.0%-34.9% | 35.1%-40.0% |
| 2 | 20.0%-29.9% | — | 35.1%-40.0% | 40.1%-50.0% | 20.0%-29.9% | 35.1%-40.0% |
| 3 | 10.0%-19.9% | — | — | 50.1%-60.0% | 10.0%-19.9% | — |
| 4 | — | — | — | 60.1%-70.0% | — | — |

*If the percentage of rays from 75° to 90° is greater than 22%, this deduction was made based on the percentage of rays from 70° to 90°.

TABLE 10

Additional parameter ranges corresponding to grade deductions.

| | Parameters | |
|---|---|---|
| Deduction | Table Dispersion [mm] | Dispersion [15°] [mm] |
| 0 | >0.022 | >0.022 |
| 1 | 0.017-0.021 | 0.017-0.021 |
| 3 | 0.011-0.016 | 0.011-0.016 |
| 5 | 0.006-0.010 | 0.006-0.010 |
| 7 | 0.000-0.005 | 0.000-0.005 |

For leakage and the percentage of rays at polar angles 45° to 75°, the larger of the two deductions is made for the measurements at different diamond orientations. For example, for diamond I, the diamond receives a deduction of 0 for the percentage of rays at polar angles 45° to 75° when the diamond is facing the source, but receives a deduction of 1 when the diamond is orientated at 15°. Accordingly, for this grading scheme, diamond 1 receives a deduction of 1 for this parameter. Deductions for each diamond, as well as the diamond's final grade are summarized in Table 11.

TABLE 11

Summary of grade deductions for diamonds I-V.

| Diamond | Spread | Table Dispersion | Table Dispersion [15°] | Rays from 45° to 75° | Rays from 45° to 75° [15°] | Leakage | Leakage [15°] | Rays from 75° to 90° | Rays from 70° to 90° | Final Score |
|---|---|---|---|---|---|---|---|---|---|---|
| I | 0 | 0 | 0 | 0 | 1 | 0 | 0 | 1 | 0 | 2 |
| II | 1 | 0 | 0 | 0 | 1 | 0 | 0 | 0 | 0 | 2 |
| III | 1 | 1 | 0 | 0 | 0 | 0 | 1 | 0 | 0 | 3 |
| IV | 0 | 1 | 0 | 0 | 0 | 0 | 0 | 0 | 0 | 1 |
| V | 1 | 1 | 0 | 0 | 0 | 0 | 0 | 0 | 0 | 2 |

The diamonds were also observed using an illumination apparatus that illuminated the diamonds with green light from polar ray directions from 0° to 45°, red light from polar ray directions from polar ray directions from 45° to 75°, and with blue light from polar ray directions from polar ray directions from 75° to about 90°. Images of the diamonds I-V acquired using the illumination apparatus are shown in FIGS. 19A-19E, respectively.

Furthermore, images were acquired with the diamonds under uniform, broadband illumination. These images are shown in FIGS. 20A-20E for diamonds I-V, respectively.

Other embodiments are within the scope of the following claims.

The invention claimed is

1. A method for imaging a gemstone, the method comprising:

illuminating a gemstone with light from different directions, wherein light incident on the gemstone from a first range of ray directions and a second range of ray directions have a first color and a second color, respectively, and the first and second ranges and first and second colors are different;

acquiring an image of the gemstone while illuminating the gemstone;

relaying said image of said gemstone to a location remote from where said image was acquired; and analyzing the image of the gemstone at said remote location to provide information related to the quality of the gemstone based on the analysis;

wherein the first range of ray directions corresponds to light incident on the gemstone from polar angles from about 45° to about 75° with respect to a hemispherical reference frame centered on the gemstone.

2. A system for imaging a gemstone comprising:

An illumination system illuminating a gemstone with light from different directions, wherein light incident on said gemstone from polar angles from about 45° to about 75° with respect to a hemispherical reference frame centered on the gemstone has a first color and light incident on the gemstone from other polar angles has a different color;

An imaging device for obtaining an image of a gemstone while illuminated;

An optical relay for transporting said image of said gemstone to a location remote from where said image was acquired; and A computer displaying said image of said gemstone at said remote location.

3. The system of claim 2 wherein said imaging device includes a CCD array.

4. The system of claim 2 wherein said imaging device includes a CMOS array.

5. The system of claim 2 wherein light incident on said gemstone from polar angles from about 75° to about 90° is a second color different from said first color.

6. The system of claim 5 wherein light incident on said gemstone from polar angles from about 0° to about 45° is a third color different from said second color and said first color.

* * * * *